(12) United States Patent
Bourn et al.

(10) Patent No.: US 6,290,382 B1
(45) Date of Patent: Sep. 18, 2001

(54) FIBER BUNDLE COMBINER AND LED ILLUMINATION SYSTEM AND METHOD

(75) Inventors: Charles T. Bourn, Minnetonka; Charles A. Lemaire, Apple Valley, both of MN (US)

(73) Assignee: PPT Vision, Inc., Eden Prairie, MN (US)

(*) Notice: Subject to any disclaimer, the term of this patent is extended or adjusted under 35 U.S.C. 154(b) by 0 days.

(21) Appl. No.: 09/135,394

(22) Filed: Aug. 17, 1998

(51) Int. Cl.[7] .................................. F21V 7/04; G02B 6/04
(52) U.S. Cl. .......................... 362/554; 362/551; 362/555; 362/558; 362/297; 362/294; 362/580
(58) Field of Search ...................................... 362/551, 554, 362/555, 581, 11, 560, 580, 297, 294; 348/131; 356/394; 385/115

(56) References Cited

U.S. PATENT DOCUMENTS

| | | | |
|---|---|---|---|
| 4,772,128 | * 9/1988 | Vinarub et al. | 356/384 |
| 4,972,093 | * 11/1990 | Cochran et al. | 250/572 |
| 5,199,091 | 3/1993 | Davenport et al. | 385/39 |
| 5,257,173 | * 10/1993 | Ohmamyuda et al. | 362/235 |
| 5,301,090 | * 4/1994 | Hed | 362/555 |
| 5,394,246 | * 2/1995 | Sugawara | 356/394 |
| 5,534,718 | * 7/1996 | Chang | 257/98 |
| 5,560,699 | 10/1996 | Davenport et al. | 362/32 |
| 5,745,176 | * 4/1998 | Lebens | 348/370 |

* cited by examiner

*Primary Examiner*—Sandra O'Shea
*Assistant Examiner*—Ali Alavi
(74) *Attorney, Agent, or Firm*—Schwegman, Lundberg, Woessner & Kluth, P.A.

(57) ABSTRACT

A fiber bundle combiner and LED illumination system and method. In one embodiment, an illumination fixture includes a plurality of light-emitting diode (LED) light sources, and a fiber-optic assembly having a common first bundle end and plurality of second ends. Each of the second ends is optically coupled to receive light from an LED. Ths fibers transmit light from the second ends to the common first end such that light from the LEDs is output at the first end. Optionally, pipe cells couple the light, wherein each LED is associated with a respective pipe cell that serves to focus light from the LED into one or more of the fibers. In one embodiment, each of the pipe cells includes a concave substantially spherical focussing reflective surface. Yet another aspect provides a method for making an LED and fiber-optic combiner assembly comprising: providing pipe cells, each pipe cell having an opening having a constriction for locating a fiber at a desired location within the pipe cell; inserting into each of the pipe cells one more more optical fibers; severing each of the optical fibers to form end at a desired position relative to the pipe cells; and assembling the plurality of pipe cells to a corresponding plurality of LEDs. In one embodiment, the severing operation includes melting the fibers to form a ball end on each fiber. In another embodiment, the assembling operation includes filling each of the pipe cells with liquid light-transmitting plastic.

27 Claims, 19 Drawing Sheets

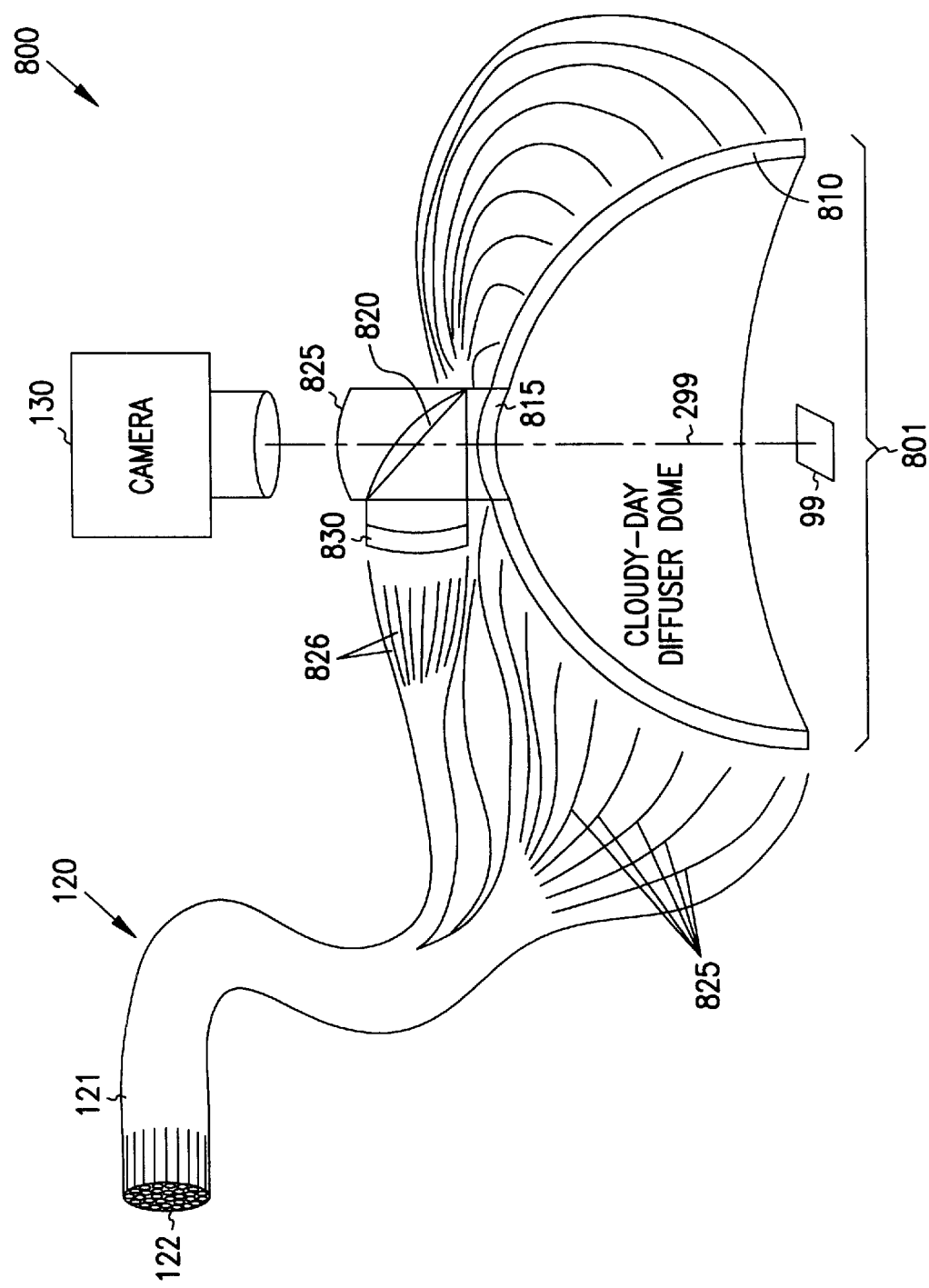

FIBER BUNDLE COMBINER AND LED ILLUMINATION SYSTEM AND METHOD

TECHNICAL FIELD OF THE INVENTION

The present invention pertains generally to illumination optics, and more particularly systems and methods for illumination of objects in machine-vision systems.

BACKGROUND OF THE INVENTION

During the manufacture of certain products, such as electrical components, it is necessary to be able to provide high-intensity illumination so that components can be thoroughly inspected with a machine-vision system. Often, the light emission head or fixture needed includes one or more light sources, for example a ring-shaped flashtube or a number of light-emitting diodes arranged along a circle or a remote light source that drives light into a number of optical fibers arranged along a circle, surrounding the lens of a video camera such that the object being imaged by the video camera is illuminated with light angled in towards the optical axis of the camera from the light fixture surrounding the lens. It is usually desirable that the light fixture or sources are arranged such that no light shines directly from the light sources into the lens.

Typically, a xenon flashtube or laser-based single-point source or other high-intensity light source (such as a halogen lamp) is used for providing light into fiber-optic-based ring head or fixture. Such systems, however, are costly, very large, inefficient, and bulky, and can interfere with the placement of other components in the machine-vision system. This is particularly troublesome when the components being measured or inspected are extremely small. Further, xenon flashtube light sources also tend to exhibit tip to about a five per cent (5%) flash-to-flash variation in intensity which makes accurate measurements of certain characteristics difficult. Single-point source systems are also generally limited to emitting light radially from only one single point, which is of limited value when shadows are problematic, such as, when inspecting a grid of electrical connectors. Specifically, light from only one or just a few point sources only illuminates the first over-sized or over-height electrical connector and, due to shadows from the first object encountered, does not provide proper illumination which would determine if other objects behind this particular first object are missing, of the incorrect size or height, or perhaps in the wrong position.

Conventional illumination systems produce a light which can be too bright in certain areas and too dim in other areas. Often, the end-result is "bloom", especially when viewing white, lightly colored, or very reflective objects which are near other objects which need to be viewed by a machine-vision camera. In order to get enough light on the other objects which need to be viewed, the aperture on the camera cannot be "stopped down" in order to prevent overexposure of the bright objects. Specifically, the area is illuminated to such an extent that the entire image appears to be the same bright saturated white color (or, if a monochromatic light source is used, saturated at whatever color is used) as viewed by the machine-vision camera and system. Such extreme brightness also poses a danger of blinding, at least temporarily, human workers nearby.

Quite often, illumination fixtures either leave certain portions of the scene in shadows, or provide too much light in certain areas, while leaving other areas with too little light. In other cases, the illumination fixture is too bulky and gets in the way of other components of the machine-vision system, associated robots, manipulators, and/or human workers.

The optimal light-source-to-optical-axis angle can vary depending on the object being inspected. One shortcoming of conventional ring light fixtures is the cost and difficulty in changing the angle between the light sources relative to the optical axis, and in changing the spread and/or focus of the light from ring-light fixture.

Thus, what is needed is a fiber-optic-based illumination system and method which is compact, well controlled, adaptable to various lighting needs, and modular so that even extremely small parts can be quickly and adequately inspected and accurately viewed or measured with a machine-vision system. Another need is to provide a compact illumination fixture, preferably one that is monochromatic. Another need is to provide a compact monochromatic LED (light-emitting diode) illumination fixture that can be quickly configured to a number of different illumination patterns remote from the LEDs. Another need is to have such an LED illumination fixture be pulsed with a relatively high-power, low duty-cycle power source.

SUMMARY OF THE INVENTION

The present invention takes advantage of the efficiency and flash controllability of high-brightness LEDs in one or more of a variety of colors, preferably arranged in a row or array, and then concentrated into a fiber-optic bundle and the properties inherent to a fiber-optic configuration to produce an illumination fixture for machine-vision systems. The present invention, in some embodiments, provides the advantages of providing monochromiiatic, efficient, stable light into a fiber-optic bundle. In some embodiments, the light is strobed in order to "stop" the movement and to concentrate the light into the time in which the shutter of the camera or the light-acquisition time of the imaging device is obtaining light.

In one embodiment, an illumination fixture for illuminating an object at a machine-vision station is provided. The fixture includes a plurality of light-emitting diode (LED) light sources, and a fiber-optic assembly having a common first bundle end and plurality of second ends. Each one of the second ends is optically coupled to receive light from one of the plurality of LEDs. The fibers transmit light from the second ends to the common first end such that light from the LEDs is output at the first end. In one Such embodiment, the common first end comprises a bundled arrangement of first ends of individual optical fibers, and wherein the second ends of each of the fibers is optically coupled to receive light from one of the plurality of LEDs. In another embodiment, each fiber at the first end terminates at a common plane. In yet another embodiment, each fiber is randomly located within the bundle at the first end.

One embodiment further includes a plurality of pipe cells, wherein each LED is associated with a respective pipe cell that serves to focus light from the LED into one or more of the fibers. In one such embodiment, each of the pipe cells includes a focussing reflective surface. In another such embodiment, each of the pipe cells includes a concave substantially spherical focussing reflective surface. In yet another such embodiment, each of the pipe cells includes a focussing lens that focusses light emitted from its LED on a fiber end.

One embodiment further includes a coupling unit attached to the first bundle end adapted to receive one of a plurality of interchanageably connected fiber-bundle head fixtures, and a fiber-bundle head fixture. Another embodiment includes a heat sink thermally coupled to the plurality of LEDs.

Another aspect of the present invention provides a method for illuminating an object at a machine-vision station. The method includes (a) emitting light from a plurality of LEDs onto individual ones of a first plurality of optical fibers; (b) forming the first plurality of optical fibers into a compact bundle having a first bundle end; and (c) coupling light from the first bundle end of the first plurality of optical fibers into a first end of a separate second plurality of optical fibers.

The method optionally includes optically coupling light from each one of the plurality of LEDs into second ends of corresponding one of the fibers is optically coupled to receive light from one of the plurality of LEDs. In other embodiments, the method includes terminating each fiber at the first end at a common plane; locating each fiber randomly within the bundle at the first end; or focussing light from each LED into one or more of the fibers using a plurality of pipe cells, wherein each LED is associated with a respective pipe cell.

Other aspects of the method coinclude providing each of the pipe cells with a focussing, reflective surface; a concave substantially spherical focussing reflective surface; and/or a focussing lens that focusses light emitted from its LED on a fiber end.

Another aspect of the present invention provides a machine-vision system for obtaining information about an object at a machine-vision station. The system includes an imaging device, an image processor coupled to the imaging device; and an illumination source coupled to the image processor. The illumination source is described above.

Yet another aspect of the present invention provides a method for making an LED and fiber-optic combiner assembly comprising: providing a plurality of pipe cells, each pipe cell having an opening having a constriction for locating a fiber at a desired location within the pipe cell; inserting into each of a plurality pipe cells one more more optical fibers; severing each of the optical fibers to form an end on each of the optical fibers at a desired position relative to the pipe cells; and assembling the plurality of pipe cells to a corresponding plurality of LEDs.

In one embodiment, the severing operation includes melting the fibers to form a ball end on each fiber. In another embodiment, the assembling operation includes filling each of the pipe cells with liquid light-transmitting plastic.

These and other features, aspects, and advantages of the present invention will become better understood with regard to the following description, appended claims and accompanying drawings.

BRIEF DESCRIPTION OF THE DRAWINGS

FIG. 8 is an isometric cross-section view of cloudy-day dome illuminator 800 according to one embodiment.

DETAILED DESCRIPTION OF THE INVENTION

In the following detailed description of the preferred embodiments, reference is made to the accompanying drawings which form a part hereof, and in which are shown, by way of illustration, specific embodiments in which the invention may be practiced. It is to be understood that other embodiments may be utilized and structural changes may be made without departing from the scope of the present invention.

The present invention provides a method and system for generating light with LEDs, coupling that light into a first fiber-optic or light-pipe bundle, and providing a coupling that allows the user to replaceably connect any one of a plurality of customized output fiber-optic bundles to the coupling. The LEDs, first fiber-optic bundle, and coupling together are packaged into a light-source box which provides cooling for the LEDs and a connection to electrical power for driving the LEDs. The output fiber-optic bundle is connected to the light-source box coupling and delivers light from the light-source box to the location where the light is needed. Various output fiber-optic bundles are customized to a length and geometry to suit particular applications.

Figure 1:
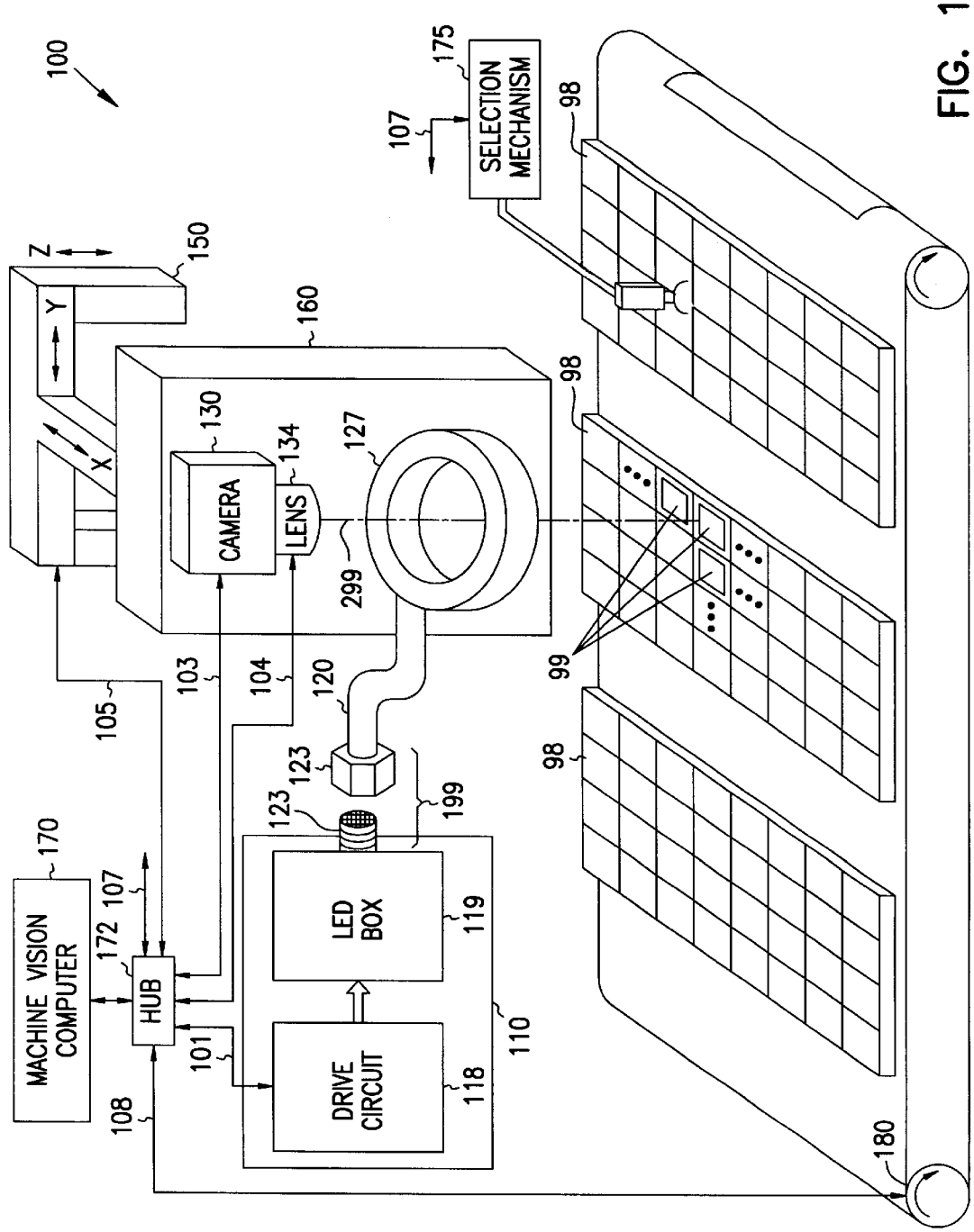
FIG. 1 is an isometric schematic diagram of one embodiment of machine-vision illumination system 100.

FIG. 1 is an isometric view schematic diagram of an embodiment of machine-vision illumination system 100 according to the present invention. In FIG. 1, an object 99 (for example, an electronics assembly, such as a ball-grid-array package 99 held in a pocketed tray 98, or a beverage can or other food or drink container, or other manufactured item moved along a manufacturing line, such as on conveyor 180) is illuminated by head 127 for inspection by a machine-vision camera (or other imaging device) 130 having lens 134, which are coupled to computer/image processor 170. In this embodiment, camera 130 is disposed to view object 99 through an opening in a ring-illumination fixture 127 which directs light downward and inward. In one exemplary system, it is desired to illuminate the top edge, inside walls and inside bottom surface of object 99 (such as a beverage container) for viewing by camera 130 with even, high intensity, short-duration illumination of a fixed predetermined intensity. In one embodiment camera 130 is a video camera, such as a Panasonic model GPMF702, having a telecentric lens 134, such as an Invaritar-brand lens made by Melles-Griot. In one such embodiment, the telecentric lens 134, which has uniform magnification across the field of view, of camera 130 is made larger in diameter than the diameter of object 99 being viewed (e.g., one embodiment uses a 6-inch diameter lens for 3-inch diameter objects) in order to reduce lens distortion, such as pin-cushioning and barrel distortion. Camera 130 is coupled to machine-vision computer 170 with suitable cables through hub 172, for example, a digital-serial link such as described in patent application Ser. No. 08/825,774 cited below, or other suitable electrical or fiber-optical signal cables. In one embodiment, camera 130 is positioned above and facing objects 99 moving by action of conveyor mechanism 180 across the camera field of view, so that camera 130 can obtain and send a captured image of object 99 to image-processing computer 170. In one embodiment, computer 170 analyzes the captured image and activates selection mechanism 175 to accept or reject each successive object (e.g., diverting rejected items into a reject bin) based on predetermined criteria, all using methods and apparatus well known to those skilled in the art of machine vision.

In the embodiment shown, machine-vision computer 170 includes image-processing capability to process and analyze the images obtained, as well as timing and control processing capability, used to send trigger pulse commands on signal connection 101 to drive circuit 118 to time the flashes of light, (in one embodiment, light intensity information is received by computer 170, also over signal connection 101); focus control commands from computer 170 are sent to lens 134 over signal connection 104, camera-control commands are sent to camera 130 over signal connection 103, translation-control commands are sent to translation element 150 over signal connection 105, selection-control commands are sent to selection mechanism 175 over signal connection 107, and conveyor-control commands are sent to conveyor mechanism 180 over signal connection 108. Conveyor mechanism 180, in various embodiments, includes a belt, rollers, and/or tray clamps to facilitate movement and placement of the objects 99 being inspected. In one embodiment, signal connections 101–108 are digital serial links, and hub 172 is a digital serial hub such as are described in patent application Ser. No. 08/825,774 cited below.

In the embodiment shown, optical head 160 hold camera 130 and illumination fixture 127 in a fixed relationship to one another, and translation element 150 (including an actuator, such as a linear actuator, and/or stepper motor, for each direction desired) moves optical head 160 in the X, Y, and/or Z directions (plus additional directions if further degrees of freedom are desired). In one embodiment, this allows conveyor system 180 to move tray 98 into position, and then stop, thus providing a stable platform holding parts 99 in an unmoving position (i.e., so there is no movement as the optical imaging and measurement is taking place). Optical head 160 is then moved to each successive position over tray 98 to take pictures of each device 99. In one such embodiment, a plurality of cameras 130 and illumination fixtures 127 are included in optical head 160 (in one embodiment, each camera is thus responsible for imaging a subset of devices, thus increasing the speed of the system; in another such embodiment, each separate camera and illumination pair is responsible for obtaining different geometric information about part 99 (e.g., one camera for 2D imaging, another for 3D imaging), thus providing additional information about parts 99 in the same amount of time).

Camera 130 is implemented as any suitable one of a number of device technologies including vidicon, CCD (charge-coupled device) line- or array-imaging devices, metal-oxide semiconductor (MOS) video cameras, and so forth. In one embodiment, camera 130 is a solid-state MOS camera having a peak wavelength sensitivity of about 550 nanometers (nm), and range of approximately 500 to 600 nm at about 97% of peak. In one embodiment, the aperture on the lens of camera 130 is suitably small in order that a relatively large depth-of-field is obtained. The type and size of lens is chosen to match the field-of-view to the size/depth of object 99. In the embodiment shown in FIG. 1, system 100 is enclosed to keep out external light.

Figure 2:
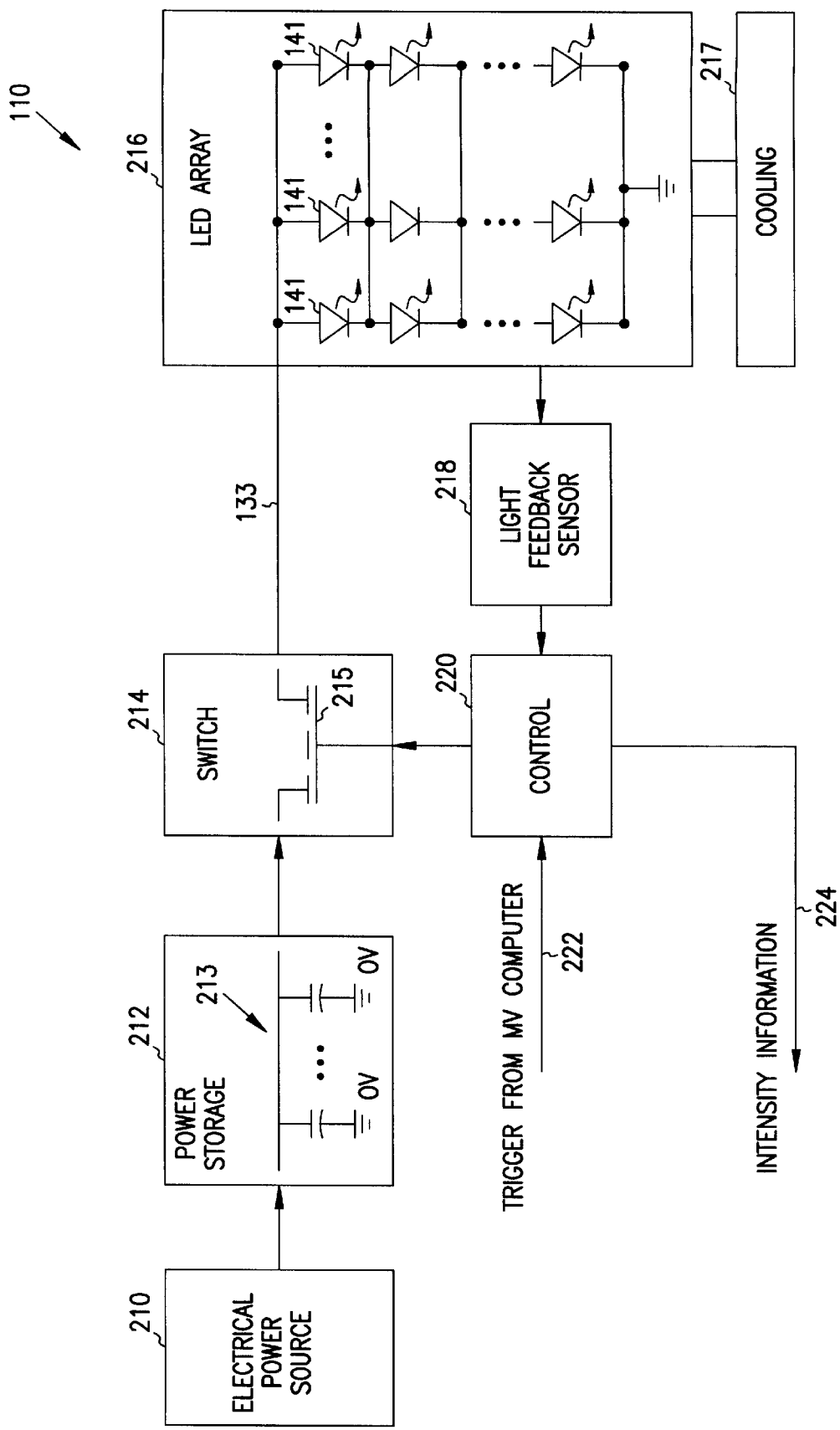
FIG. 2 is a circuit schematic diagram of an LED source 10 portion of one embodiment of machine-vision illumination system 100.

In one embodiment, shown in FIG. 2 (FIG. 2 is a circuit schematic diagram of a portion of one embodiment of machine-vision illumination system 100), each light box 110 is connected to (or includes) an electrical power source 210 (such as a battery or AC-to-DC power supply), a power-storage circuit 212 (such as a capacitor box having a plurality of capacitors wired in parallel to ground), which is connected to a power switch 214 that is driven by control circuit 220 which is connected to image processor 170. The charge on capacitor box 212 is discharged through LED arrays 216 in light box 110 when computer 170 drives a pulse-trigger command on signal cable 222 which in turn drives power MOSFET (metal-oxide-semiconductor field-effect transistor) 215 to substantially short. (In other embodiments, a bipolar transistor is used instead of MOSFET 215, in order to better control a variable amount of current.) In one embodiment, a short-duration pulse (approximately 10 microseconds to 100 microseconds long) is used to provide a short, intense pulse of light. Further details of power supply 210 and capacitor box 213 are found on Ser. No. 08/532,213 cited below. In one such embodiment, a photo detector 218 is used to detect the light output and provides intensity information feedback to computer 170 which is used to control the intensity, duration, and/or frequency of the light pulses or the electronic shuttering of camera 130. In one embodiment, LED array 216 includes a plurality of individual LEDs 141 wired in a parallel-series configuration, and cooling unit 217 is implemented as a heatsink, thermally coupled to the LEDs 141, with a fan blowing onto the heatsink.

Cooling unit 217 provides a low-thermal-resistance sink for heat generated by the large number of LEDs 141 each coupled into one or more individual fibers 115. The cooling unit 217 and LEDs 141 can be distributed over as large an area as convenient to dissipate the waste heat, and yet the fibers can condense the light into a bundle with a relatively small cross section, and transport the light to a convenient coupling point 199 (see FIG. 1). Coupling point 199 allows the interchange of light boxes 110 and/or light-head fixtures 120, such that a single light box 110 can be coupled to a variety of different light-head fixtures 120 to suit the different light distribution patterns desired (e.g., ring light versus linear source versus spot source versus cloudy-day distribution), or a single light-head fixture 120 can be coupled to a variety of different light boxes 110 to suit the different light source characteristics desired (e.g., LEDs versus xenon versus halogen incandescent, and pulsed versus continuous output). By having a common coupling point design, the designers of the light boxes 110 need only be concerned with aspects up to the coupling point, and the designers of the light-head fixtures 12 need only be concerned with aspects after the coupling point.

Thus, in one embodiment, the LEDs 216 are powered to provide one or a series of short light pulses or strobed illumination for a machine-vision camera. In one such embodiment, pulses of varying intensity are used, wherein a very bright pulse is used to illuminate dim objects, followed by a less-bright pulse for more reflective portions of the field of view. In another such embodiment, a single pulse is shaped to have different intensities during different portions of the same pulse, and the camera or cameras are controlled to obtain two or more images from different moments of time of the single shaped pulse.

In another embodiment, the LEDs are powered to provide a non-strobed, varying-over-time, or constant illumination. In one such embodiment, using a photodetector to measure intensity (or using intensity information from the captured image from the camera), the illumination is varied in intensity over time to achieve a desired intensity profile (for example, to achieve bright illumination for dim or non-reflective objects, and less-bright illumination for more reflective objects) and in other embodiments, the intensity is kept constant.

In one embodiment, LEDs 141 are high-brightness red LEDs 1200 millicandles (mcd) at a peak wavelength of approximately 621 nm., for example, HLMA-KH00-type T1-sized lights having a half-angle of approximately 22.5° available from Hewlett-Packard. In other embodiments, green, blue, or ultra-violet LEDs (such as are available from Nichia Chemical Industries of Japan) are used. In another embodiment, a Toshiba part number TLRH160 emitting red light (644 nm at 1800 typical mcd) with a 5-degree half angle is used), spaced as closely as possible in a row. In other embodiments, other LEDs having different colors/wavelengths, half-angles, intensity, or power capabilities are used. In one such embodiment, LED light source 110 is configured to be replaced/changed in order to let the user choose a suitable combination of colors/wavelengths, half-angles, intensity, or power capabilities for a particular application.

Figure 3:
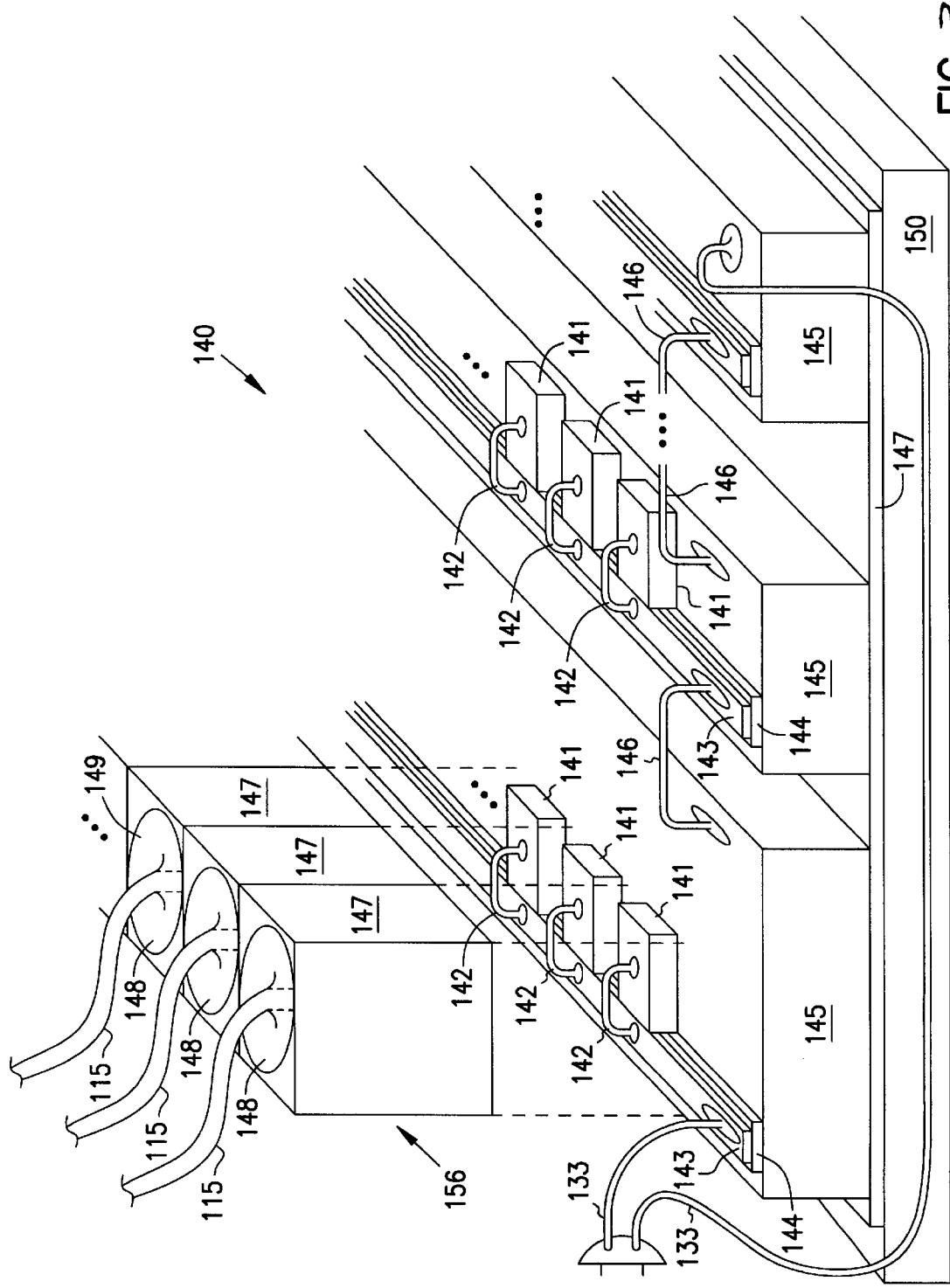
FIG. 3 is an exploded isometric view of LED illumination source 140 according to one embodiment of the present invention.

FIG. 3 is an exploded isometric view of LED illumination source 140 according to one embodiment of the present invention. A plurality of LED chips 141 are attached to strip block 145 which is thermally and electrically conductive (e.g., aluminum is used in one embodiment, and tinned copper is used in another embodiment). Strip block 145 provides a thermal conduction path from the bottom of each LED chip, as well as an electrical connection for a row of LED chips wired in parallel. Insulator strip 144 (made from, e.g., polyamide, silicon oxide (glass), or ceramic), and conductor 143 (e.g., aluminum is used in one embodiment, and tinned copper is used in another embodiment) are placed on strip block 145, and run parallel to the row of LED chips 141 on strip block 145. Wire bonds 142 (e.g., gold wires) are ultrasonically bonded to each LED chip 141 and to conductor 143, thus wiring each row of LED chips in parallel. Wire bond 146 wires each block strip 145 in series with the next conductor 143. Input wires 133 couple to the first conductor 143 and to the last block strip 145. A thin layer 151 of electrically insulating material, such as polyamide, silicon oxide, or ceramic, is deposited between the plurality of block strips 145 and lower heatsink 150. In the embodiment shown, the LEDs are wired in a series-parallel configuration as shown in block 216 of FIG. 2. In another embodiment, only a single block strip 145 is used, the LEDs are wired in a parallel configuration, and in one such embodiment, no insulating layer 151 or lower heatsink 150 are needed or used.

FIG. 3 also shows a single coupling strip 156 that has a plurality of pipe cells 147, each pipe cell 147 having a through-opening 148. One or more individual fibers 115 is inserted into opening 148, which serves to position the fibers to receive light from LEDs 141. In one embodiment, the fibers are inserted into the openings 148, fixed in place using a suitable light-transmitting potting epoxy (or other clear plastic), and melted or cut to the desired length (i.e., it is desirable to have every fiber positioned to the same depth in each respective pipe cell 147, and thus they are cut or melted to length after every fiber is inserted and fixed in place). In the embodiment shown in FIG. 3, the strips 156 are linear strips, which makes threading the fibers into openings 148 somewhat simpler. A plurality of such linear strips, once the fibers are loaded, fixed in place and cut, are then aggregated into a two-dimensional array which is then inverted, filled with potting plastic, and attached to the array of LED chips 141.

Figure 4A:
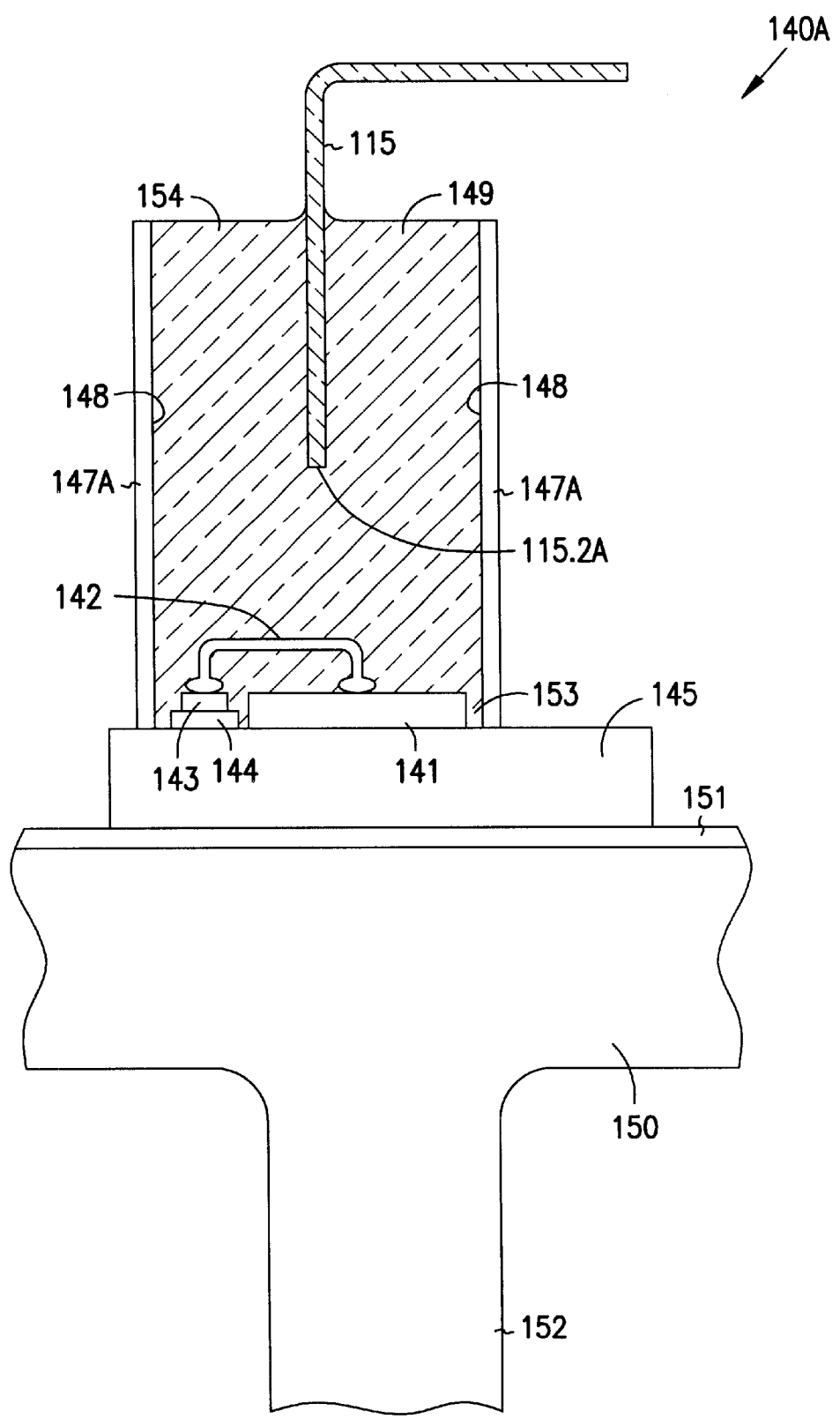
FIG. 4A is a cross-section view of one LED of LED illumination source 140A of one embodiment.

FIG. 4A is a cross-section view of one LED of LED illumination source 140A of one embodiment. Each LED chip 141 is optically coupled to one or more optical fibers 115. In one embodiment, a strip 156 (see FIG. 3) of hollow, parallel, rectangular pipe cells 147 (made from any suitable material such as molded plastic or metal) are placed so that one open end 153 of each pipe cell 147 is disposed over one LED chip 141, and one or more optical fibers 115 are inserted into the other open end 154. In other embodiments, the inner cross-section of pipe cells 147 are suitable shapes other than rectangular, such as circular, in order that light reflected from their inner surface is focussed into fiber 115.

The pipe cells 147 serve to position the fibers 115 next to the LEDs 141, to maintain such an optimal positioning, and to focus and transmit the light from the LEDs 141 into the fibers 115.

In the embodiments shown, optical fibers 115 of optical bundle 111 contemplate using one or more individual light-transmitting fibers made of plastic or glass or other suitable material. In some embodiments, each fiber is clad with a material having a different index of refraction, in order to better reflect light inside the fiber, in order to transport as much light as possible from one end of the fiber to the other. In other embodiments of the present invention, optical fibers of the embodiments shown are replaced by light pipes (which in some embodiments are cast from plastic, and in other embodiments are sliced from a suitable plastic material). In some embodiments, the cladding is removed from an area near the tip of the fiber 115 that is placed nearest to the LEDs, in order to allow more light to enter the fiber 115.

The inside surface 148 of the opening in each pipe cell 147 is made highly reflective (e.g., by coating with vacuum-deposited aluminum), and each is filled with a transmissive (i.e., highly light transmissive at the wavelength of the LEDs 141) material 149 such as plastic. In one embodiment, transmissive material 149 is selected to have an index of refraction to closely match the index of refraction of optical fiber 115, in order to minimize the light that might otherwise be reflected at the interface between fiber 115 and transmissive material 149 were their respective indexes of refraction different.

Figure 4B:
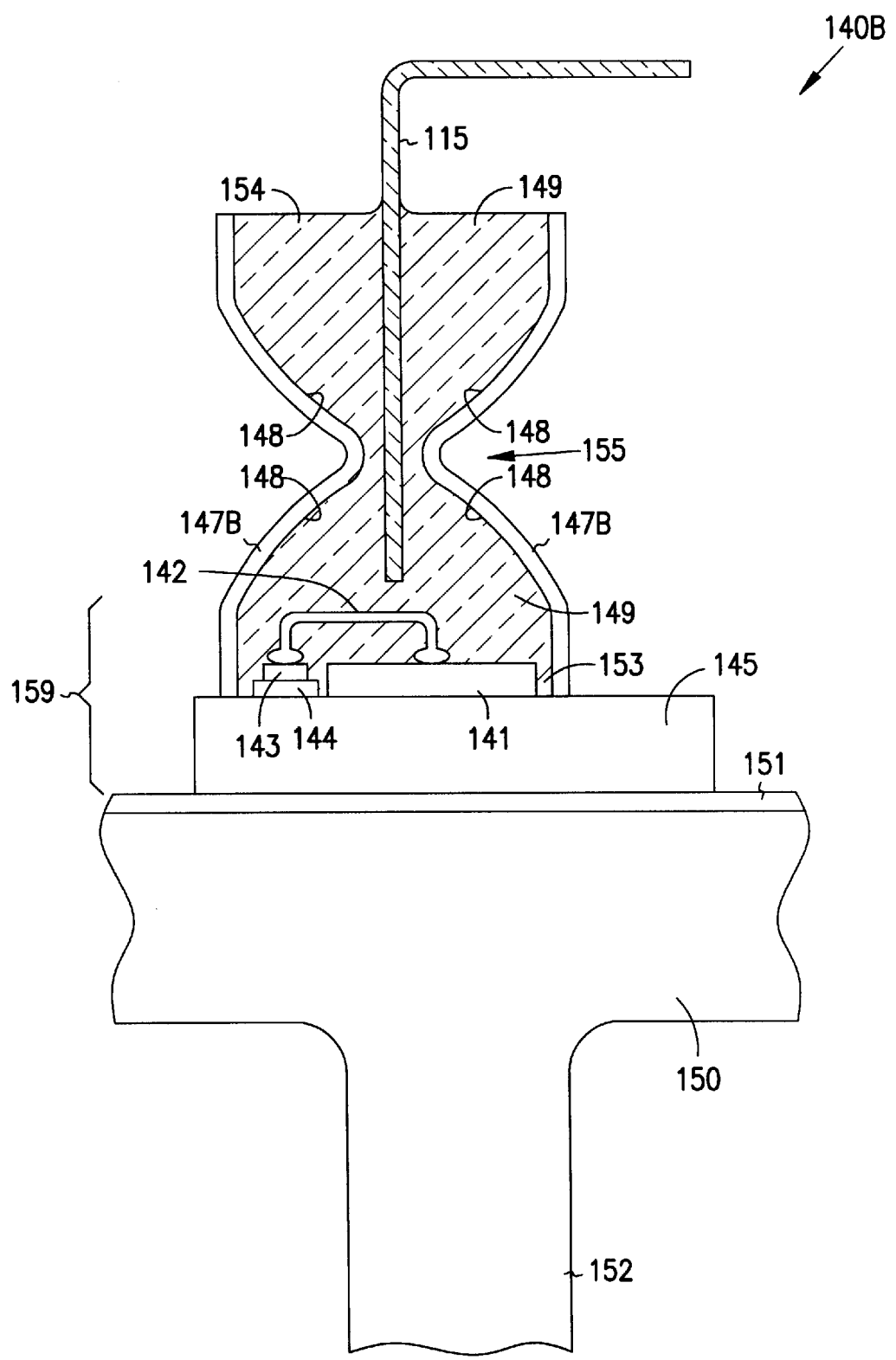
FIG. 4B is a cross-section view of one LED of LED illumination source 140B of another embodiment.

In some embodiments of illumination source 140, such as 140B shown in FIG. 4B (which is otherwise the same as FIG. 4A), each one of the plurality of pipe cells 147B has an opening that is tapered from an inner diameter (at the lower open end of pipe cell 147B drawing of FIG. 4B) that is large enough to accommodate LED chip 141 and its wiring 142, to a smaller inner diameter just large enough to easily accommodate optical fiber 115 and to hold fiber 115 at the focus of the light from the LED 141. In one embodiment, the taper is then reversed, (and opens up at the top end as shown in FIG. 4B), in order to make it easier to thread the optical fiber 115 into the top end of tapered pipe cell 147B. (That is, if the end 154 was very small, i.e, if constriction 155 was at end 154, is would be more difficult to inert fiber 115 into that hole than for the configuration shown in FIG. 4B.) In one embodiment, the lower taper (the taper nearest LED chip 141) has a circular horizontal cross section, and a vertical cross section that is a curved (e.g., parabolic) shape chosen to focus the light generally emitted in a upward vertical direction from LED chip 141 (with reference to FIG. 4B), such that this light is reflected from reflective surface 148 and into optical fiber 115.

The taper at end 153 of pipe cell 147B provides two advantages: it provides a focussing of light that is vertically emitted from LED 141 by reflecting it into fiber 115, and its constriction 155 in the middle allows the manufacturer to:

- position strip 156 and thus pipe cell 147B with end 153 in the upward direction,
- insert the fiber 115 from the bottom through end 154 and through the constriction 155 (thus blocking much or all of the remaining opening in constriction 155),
- (optionally) fill ends 154 with a liquid plastic material that then sets,
- cut (e.g., with a knife edge) or melt (e.g., with a laser beam or flame) the ends of every fiber such that the proper or desired amount of the fiber tip is within the focal area of the pipe cell 147 including any lens associated with the LEDs,
- fill end 153 with a liquid phase of transmissive material 149 (e.g., plastic or epoxy)(which will not flow out the other end 154 due to the constriction 155 and fiber 115, or due to the solidified plastic from the previous steps), and
- place the LED assembly 159 (i.e., LED chip 141, wire 142, conductor 143, insulator 144, and strip block 145 (plus insulator 151 and heatsink 150, if desired)) into the liquid transmissive material 149, which is then allowed to set or solidify, thus sealing the electronics of the LED assembly 159 from the external environment, and optically coupling LED 141 to fiber 115. In one embodiment, the LED assembly 159 of a single strip block 145 and its row of LED chips 141 are sealed to a single strip 156 of pipe cells 147, in order to simplify manufacture. This sealing assembly step is repeated for all strip blocks 145, and the plurality of strip blocks is then attached to insulator 151 and heatsink 150, resulting in the configuration as shown in FIG. 3.

In some embodiments, the opening in pipe cell 147B is circularly symmetric in the horizontal direction, having the vertical cross-section substantially as shown. In some embodiments, the vertical cross section has a spherical or paraboloid shape to focus the light that is emitted in a generally upward direction (i.e., upward and vertical are relative to the drawing shown, and do not necessarily represent the orientation of the box while being assembled or used) onto the tip and nearby regions of the end of fiber 115. In one embodiment, the end 1 to 2 millimeters (mm) of the fiber represent the focal region of the pipe cell 147.

Figure 4C:
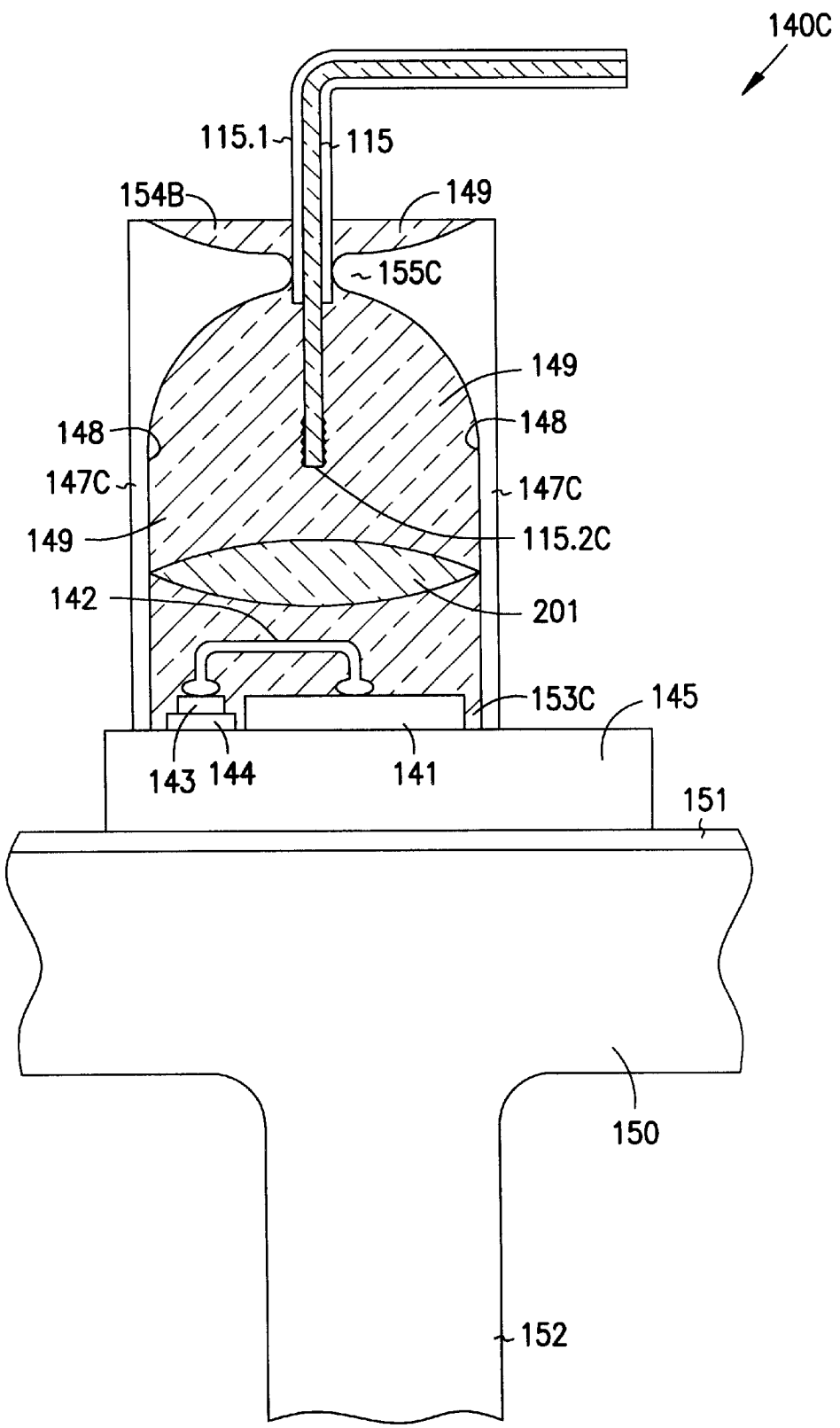
FIG. 4C is a cross-section view of one LED of LED illumination source 140C of yet another embodiment.

FIG. 4C is a cross-section view of one LED of LED illumination source 140C of yet another embodiment. FIG. 4C shows several individual features which can be combined singly or in combination with any of FIGS. 4A–4H. In FIG. 4C, fiber 115 is shown with a cladding 115.1 that enhances keeping the light within the fiber 115 (by total internal reflection. Also shown in FIG. 4C, the cladding 115.1 is removed near the end of fiber 115 to facilitate entry of light through the sides of the fiber, and the sidewall 115.2C near the end of the fiber 115 is roughened or textured (by, for example, mechanical abrasion or chemical etching) such that light incident to the sides via reflection from the upper end of the opening 153 is scattered to better enter the fiber rather than just passing through. Further, lens 201, which has a higher index of refraction (for convex lenses) than transparent potting 149, acts to focus direct light from LED 141 into the end of fiber 115. Constriction 155C between upper opening 154C and lower opening 153C acts to hold fiber 115 in the center of the focus of pipe cell 147.

Figure 4D:
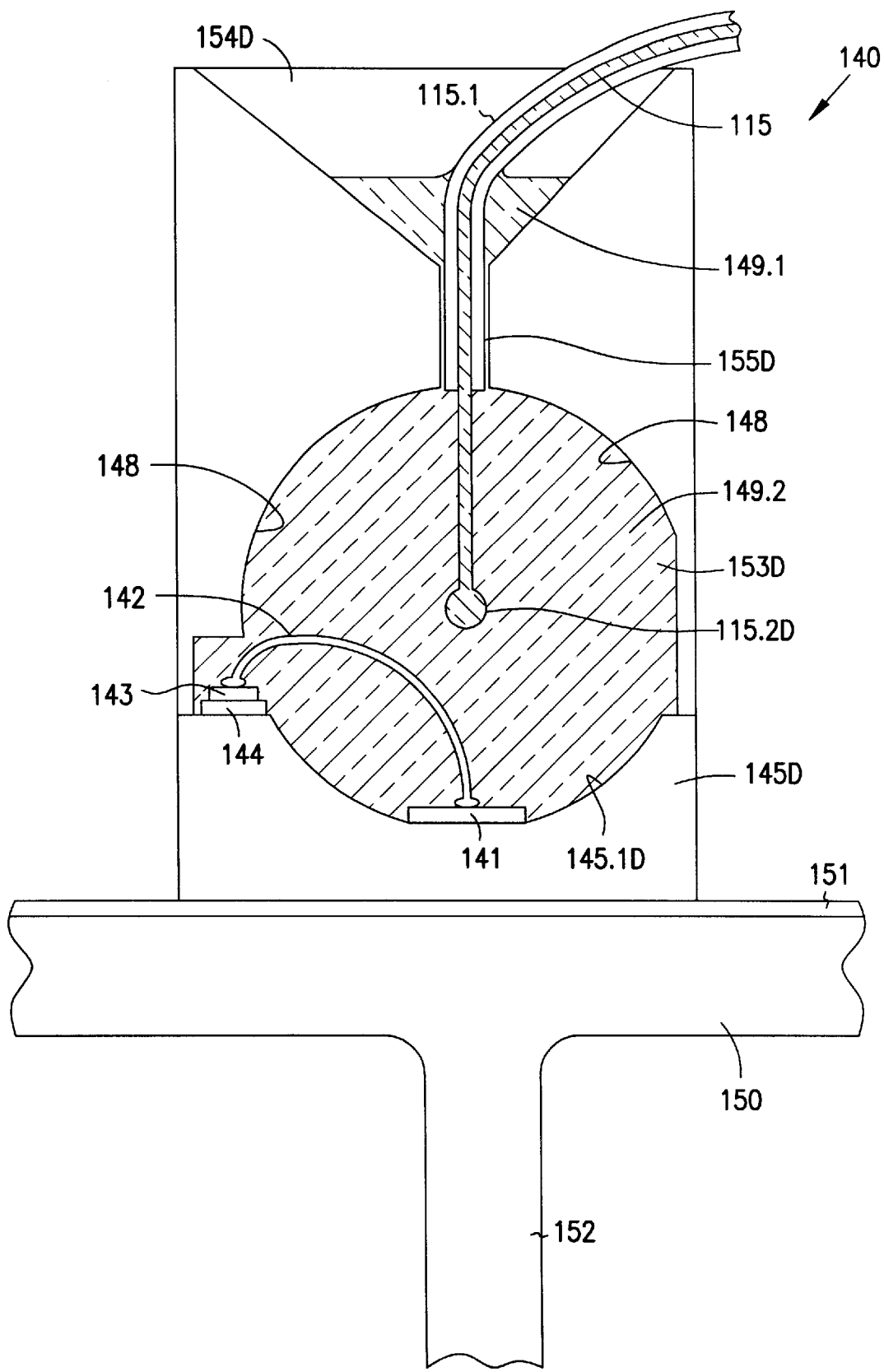
FIG. 4D is a cross-section view of one LED of LED illumination source 140D of still another embodiment.

FIG. 4D is a cross-section view of one LED cell of LED illumination source 140D of still another embodiment. In FIG. 4D, a number of advantageous aspect of the present invention are shown. Strip block 145D is formed with a row of conical, spherical, or paraboloid depressions 145.1D which form a reflecting focussing element to direct light from LED 141 onto the end of fiber 115 (the cross section of one such depression 145.1D is shown). Lower-end opening 153D is also formed as a reflecting focussing element, having a conical, spherical, or paraboloid reflecting surface 148. Constriction 155D is elongated, in order to center fiber 115. Cladding 115.1 is removed from a portion of the end of fiber 115.

In one embodiment, the fiber is inserted through constriction 155D via funnel-shaped opening 154D which has an enlarged upper end to facilitate threading fiber 115. A plastic potting 149.1 is then injected, and allowed to set to fix fiber 115 in place. A selective etch is then used to remove cladding 115.1 from the portion of fiber 115 that is within cavity 153D. A laser beam is then directed at the end of every fiber in a strip block 156, which melts the fibers, simultaneously severing them at the proper depth and forming a ball end 115.2D which becomes a small lens to admit more light. The cavities 153D are then filled (or overfilled) with liquid light-transmitting plastic and then joined against the assembly of LED 141, wire 142, and conductor strip 143, strip block 145D, to form the sealed structure shown in cross section in FIG. 4D. Strip block 145 and heat sink 150 conduct heat from LED 141 to fins 152. In other embodiments, various individual features of this FIG. 4D embodiment are combined with other features of FIGS. 4A–4H.

Figure 4E:
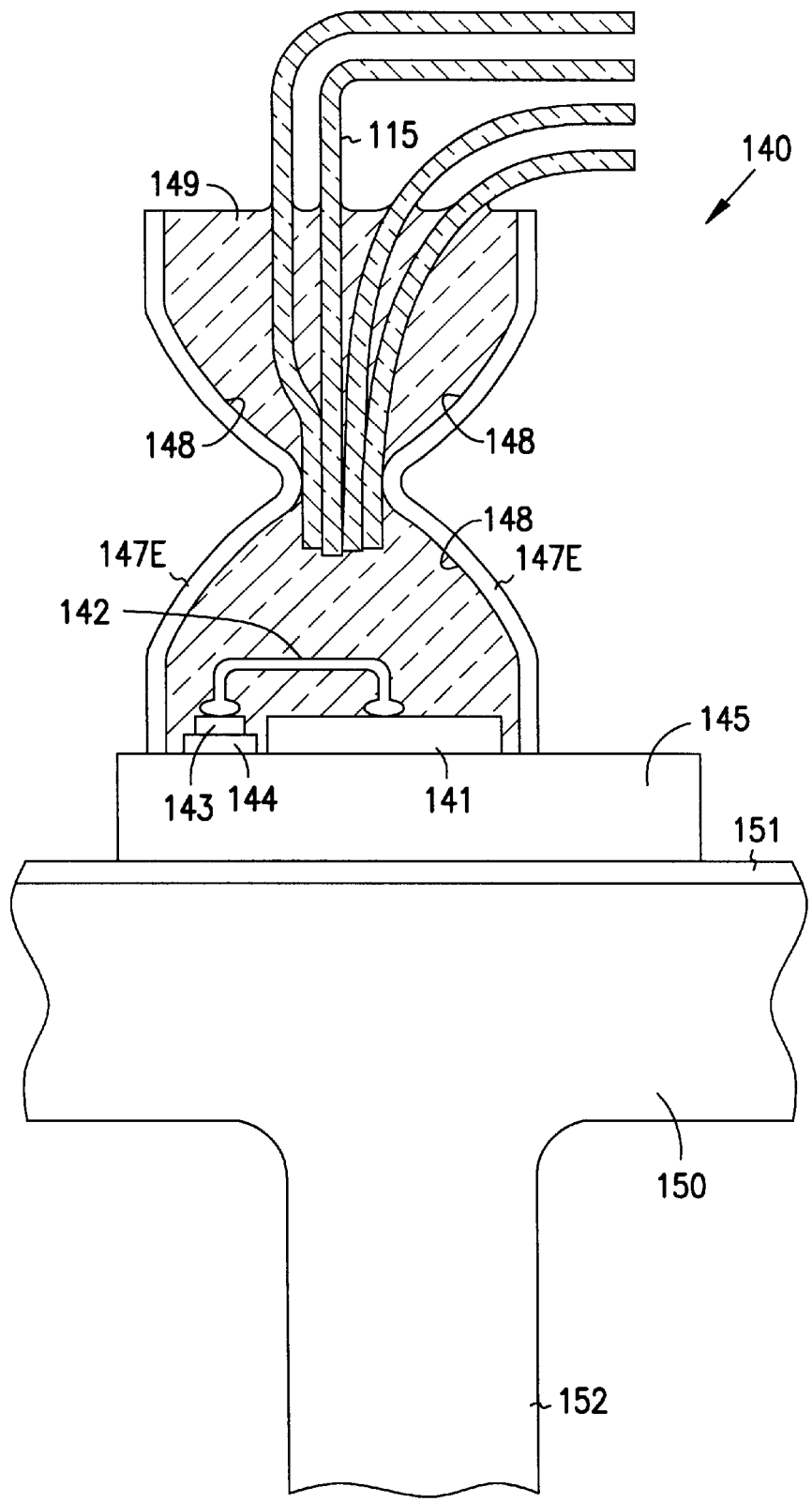
FIG. 4E is a cross-section view of one LED of LED illumination source 140E of another embodiment.

FIG. 4E is a cross-section view of one LED of LED illumination source 140E of another embodiment. This embodiment, which is otherwise similar to the above descriptions, includes a plurality of fibers 115 into a pipe cell 147E.

Figure 4F:
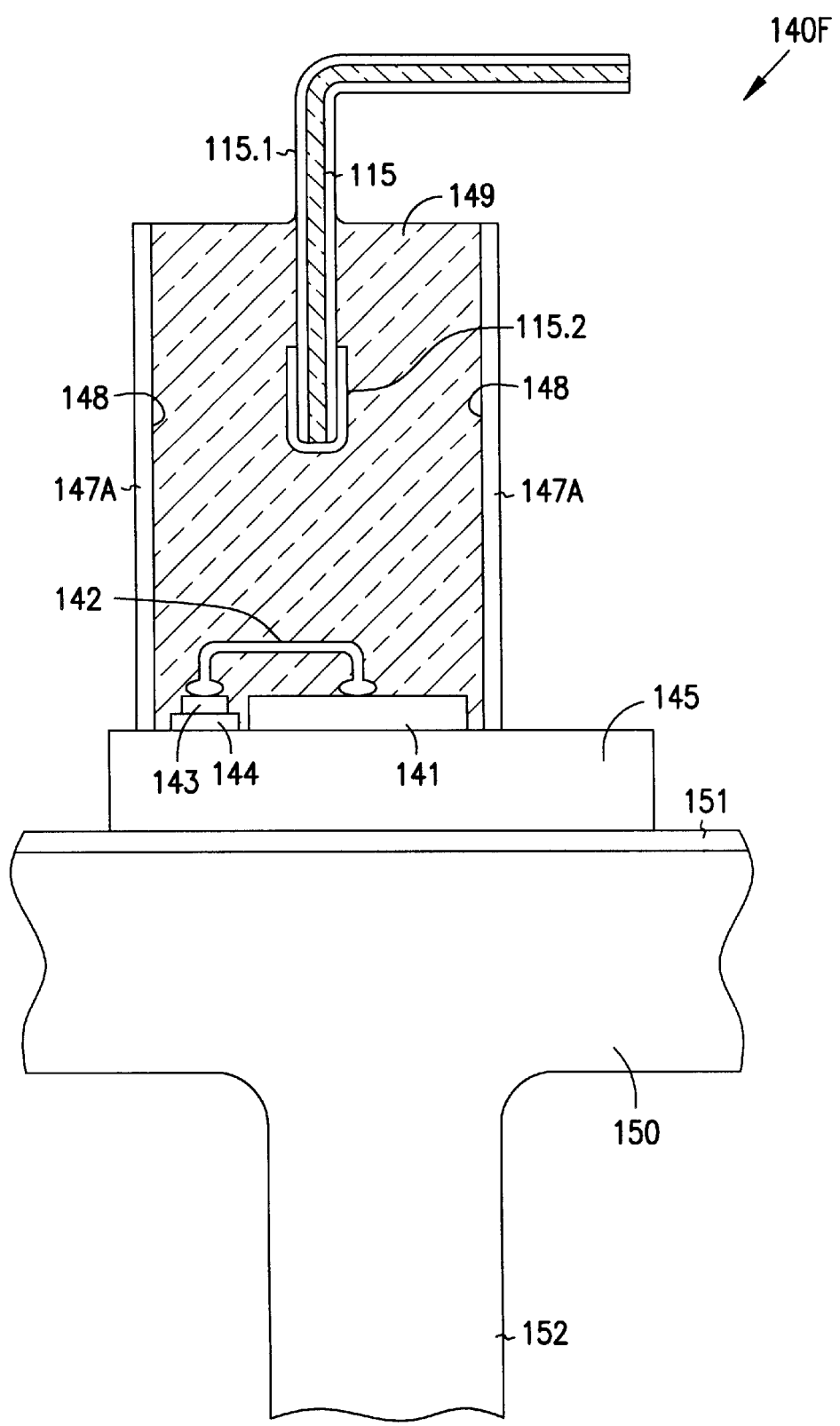
FIG. 4F is a cross-section view of one LED of LED illumination source 140F of another embodiment.

FIG. 4F is a cross-section view of one LED of LED illumination source 140F of another embodiment. This embodiment, which is otherwise similar to the above descriptions, includes a coating 115.2 having a thickness, shape, and an index of refraction empirically chosen to enhance light capture into the end of fiber 115.

Figure 4G:
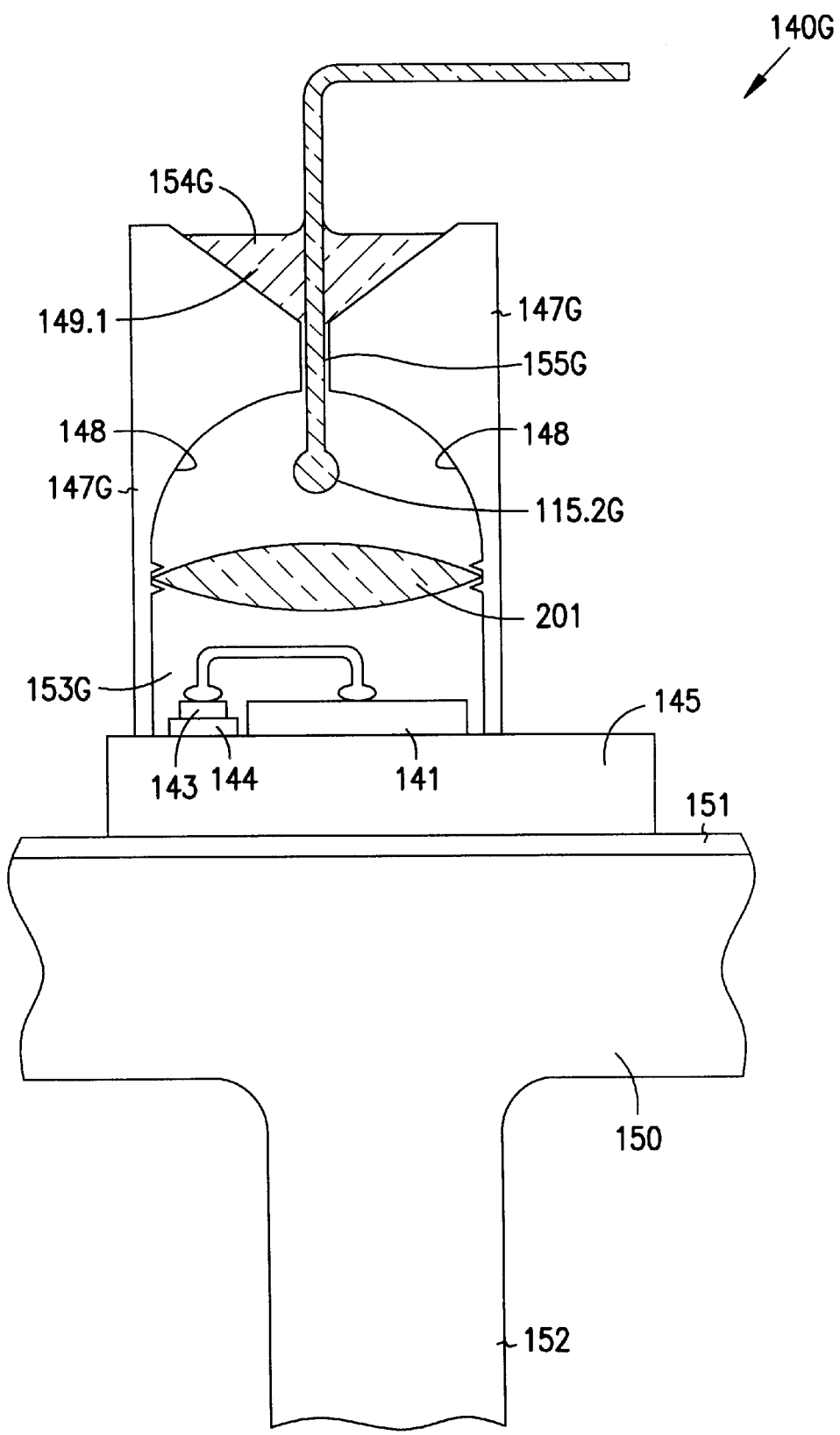
FIG. 4G is a cross-section view of one LED of LED illumination source 140G of another embodiment.

FIG. 4G is a cross-section view of one LED of LED illumination source 140G of another embodiment. In this embodiment, no potting 149 is used within cavity 153G. Lens 201 focusses light onto ball end 115.2G as described above. Potting 149.1 hold fiber 115 in place as describe above. Spherical reflective surface 148 also focusses light onto fiber ball end 115.2G.

Figure 4H:
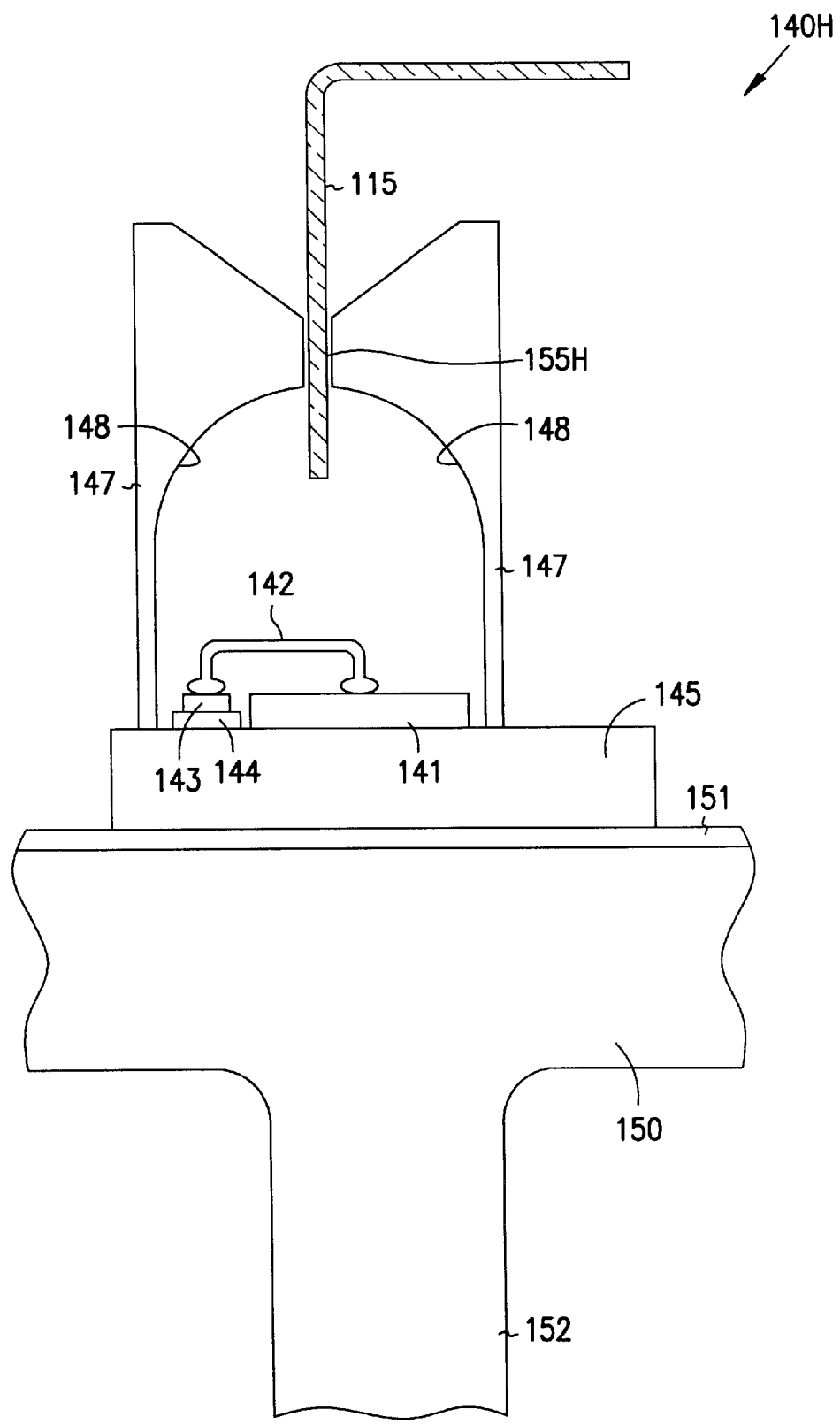
FIG. 4H is a cross-section view of one LED of LED illumination source 140H of another embodiment.

FIG. 4H is a cross-section view of one LED of LED illumination source 140H of another embodiment. In this embodiment, fiber 115 is press-fit into constriction 155H. Spherical reflective surface 148 also focusses light onto flat-cut fiber end 115.2H.

Figure 5:
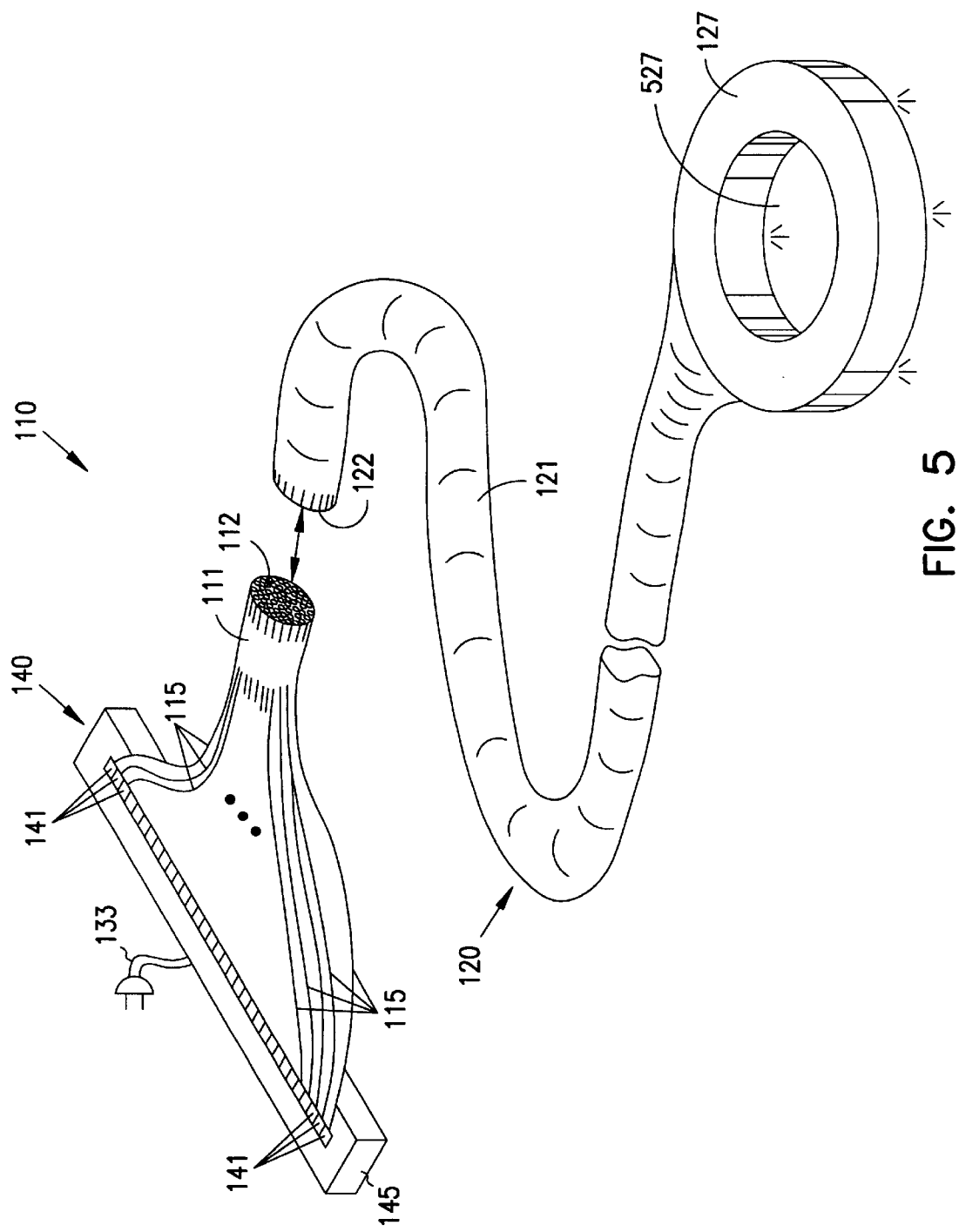
FIG. 5 is an exploded isometric view of LED light box 110 and fiber-optic bundle 120 according to one embodiment.

FIG. 5 is an exploded isometric view of the contents of LED light box 110 and output fiber-optic bundle 120 according to one embodiment. In this embodiment, LED assembly 140 includes only a single strip block 145 and its associated row of LEDs 141 (as detailed above in FIGS. 3, and 4A or 4B), which are optically coupled to a plurality of optical fibers 115, which are then grouped into a fiber bundle 111 having light output end 112. Electrical cable 133 provides power to the LEDs 141. One purpose for ending fiber bundle at light output end 112 is so that any one of a plurality of different light output bundles 120 may be interchangeably connected to light box 110. In the embodiment shown, light output bundle 120 includes a light input end 122, a fiber bundle 121 of suitable length (some typical applications use a length of 3 to 20 meters for fiber bundle 121, in order to deliver light from where the light box 110 is located to the factory-floor location where the light is needed; this allows isolation from the electrical noise and/or heat associated with driving LEDs 141 at high power), and a light-output head 127 which, in this embodiment, is a ring-light head that allows illumination of a device under test from all circumferential directions, while leaving a circular central opening 527 through which camera 130 can obtain images of devices 99 (see FIG. 1).

In one embodiment, the individual fibers are randomized in the bundle (i.e., the fibers leading from consecutive LEDs 141, or LEDs 141 from one area, are distributed randomly across the rest of the fibers in the bundle), in order to even out (i.e., homogenize) the illumination provided. In one such embodiment, it is the fibers in bundle 112 in illumination source 110 that are randomized. In another such embodiment, it is the fibers in bundle 122 in fiber bundle 120 that are randomized. In yet another embodiment, both bundles are randomized independently.

Figure 6:
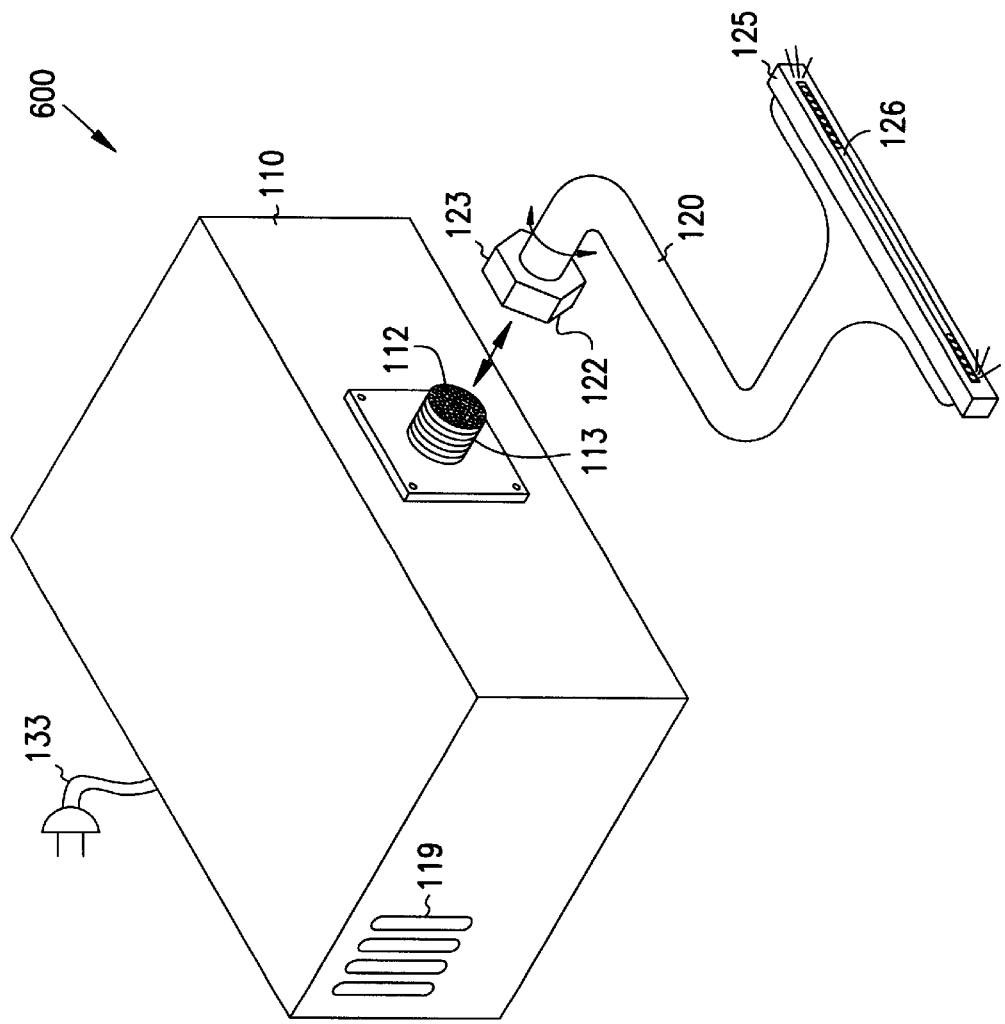
FIG. 6 is an isometric view of LED light box 110 and fiber-optic bundle 120 according to another embodiment.

FIG. 6 is an isometric view of LED light box 110 and fiber-optic bundle 120 according to another embodiment (denoted illumination system 600). Light box 110 shown includes a threaded coupling 113 for connecting any one of output fiber bundles 120 (e.g., any of those shown in FIGS. 1, 5, 6, or 8). Light output end 112 of fiber bundle 112 is presented through a central opening of threaded coupling 113. Air circulation holes 119 assist in cooling of the LEDs 141 contained within light box 110. Cable 133 provides the electrical power and/or trigger signal for causing the LEDs to emit light. In the embodiment shown, output fiber bundle 120 has a hex-nut having a female threaded connector 123 adapted to connect to connector 113 of light box 110. This allows interchangeability of output fiber bundles 120 between conventional incandescent-powered light boxes having a matching connector and the LED-powered light boxes of the present invention. Output head 125 of FIG. 6 includes a substantially straight linear arrangement of output ends 126 of the fibers of output bundle 121. Such an output head is useful in situations where a high-powered sharp line light source is desired. Output bundle 121 is typically enclosed in a rugged opaque covering suitable for a factory environment.

In another embodiment, the coupling between fiber bundle 112 and fiber bundle 122 is formed by placing fiber bundle 112 at a female fitting and fiber bundle 122 at a male fitting. In one such embodiment, the female and male fittings are each provided with a highly reflective or mirror-like cylindrical surface in order to transfer as much light as possible into fiber bundle 122. In one such embodiment, the numerical apertures of both fiber bundle 112 and fiber bundle 122 are each adjusted to transfer as much light as possible into fiber bundle 122.

Figure 7:
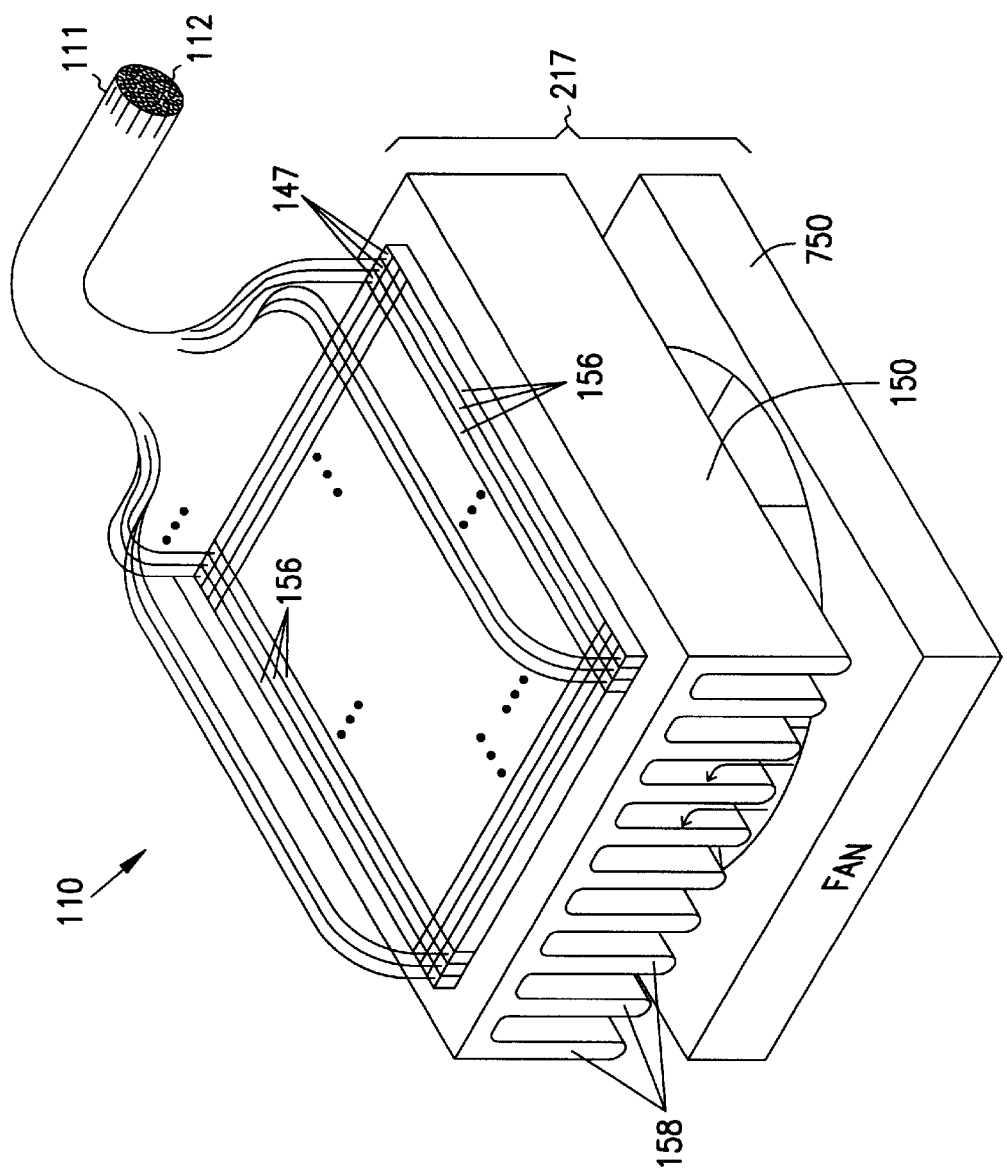
FIG. 7 is an isometric view of LED light box 10 according to one embodiment.
Figure 9A:
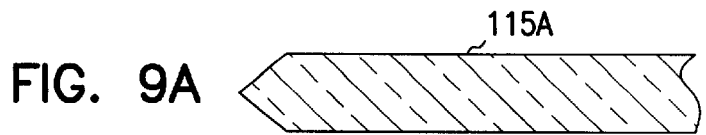
FIGS. 9A–9H are cross-section views of the tip treatments of fiber ends 115A–115H respectively of various embodiments.
Figure 9B:
Figure 9C:
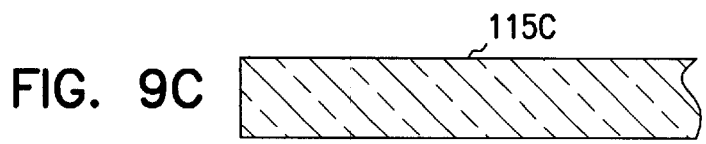
Figure 9D:
Figure 9E:
Figure 9F:
Figure 9G:
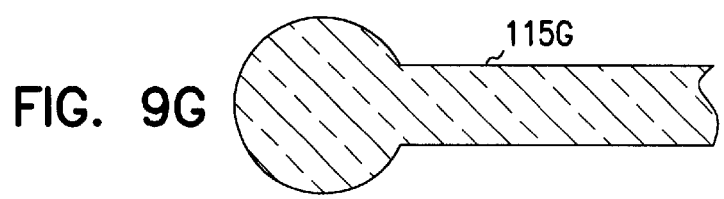
Figure 9H:

FIG. 7 is an isometric view of the contents of LED light box 110 according to one embodiment of the present invention. In this embodiment, a rectangular array configuration of LEDs is provided. The rectangular array of one embodiment includes a plurality of strip blocks 156 assembled side-by-side on an insulated heatsink 150 having a plurality of fins 158. In another embodiment, a single rectangular array block having a rectangular or hexagonal or other grid pattern of cells 147 replaces the plurality of strip blocks 156 just described. A fan 750 blows cooling air that impinges on the fins 158. The individual fibers 115 are gathered into a compact bundle 111 having a coupling end 112. In one embodiment, the fibers are randomized on their position within bundle 111 near and at end 112, in order to even the light intensity over the end 112. Other aspects of FIG. 7 are as described above for FIGS. 3 and 4A/4B.

FIG. 8 is an isometric cross-section view of cloudy-day dome illuminator fixture 800 according to one embodiment. In this embodiment, output fiber bundle 121 transmits light from input end 122 to diffuser head 801. Diffuser dome 810 is constructed of a translucent material such as milky glass or plastic. Individual fibers 825 of fiber bundle 121 are distributed around and over the outside surface of diffuser dome 810 in order to produce diffuse, shadowless light on device 99. Optical axis 299 of camera 130 passes through an opening 815 in dome 810. a beamsplitter 820 directs light from secondary diffuser 830 to fill in the space of opening 815. Such an opening would otherwise produce a dark spot in the otherwise diffuse omnidirectional light. In one embodiment, beamsplitter 820 is a 50—50 beamsplitter (passing ½ and reflecting ½ of the incoming light). Tube 825 has an anti-reflective coating (i.e., black at the wavelength of the LED light), such that light from diffuser 830 that gets transmitted by beamsplitter 820 is then absorbed rather than disbursed to camera 130. The number of fibers 826 per unit area that supply light to secondary diffuser 830 is higher than the number of fibers 825 per unit area that supply light to diffuser dome 810, in order that the diffuse light through opening 815 is of the same intensity as the rest of dome 810 (such light is otherwise reduced by the additional distance to secondary diffuser 830 and the 50—50 splitting effects of beamsplitter 820.

FIGS. 9A–9H are cross-section views of the tip treatments of fiber ends 115A–115H respectively of various embodiments. Fiber end 115A of FIG. 9A has a blunt conical end on fiber 115. Fiber end 115B of FIG. 9B has a sharp conical end on fiber 115. Fiber end 115C of FIG. 9C has a flat cut end on fiber 115. Fiber end 115D of FIG. 9D has an angled cut end on fiber 115. Fiber end 115E of FIG. 9E has a concave (i.e., lensed) end on fiber 115. In one embodiment, the fiber end 115E is formed by melting the fiber end against a spherical mold. Fiber end 115F of FIG. 9F has a convex (i.e., lensed) end on fiber 115. In one embodiment, the fiber end 115F is formed by melting the fiber end against a concave mold. Fiber end 115G of FIG. 9G has a spherical rounded end on fiber 115. In one embodiment, fiber end 115G is formed by melting the end of fiber 115 with a flame or with laser energy. Fiber end 115H of FIG. 9H has a textured or rough surface end on fiber 115. In one embodiment, fiber end 115H is formed by chemical etching (e.g., using hydrofluoric acid on a glass fiber). In another embodiment, mechanical abrasion machining is used. In one such embodiment (see FIG. 4C above) the tip of fiber 115H is smoothed of polished (e.g., by cutting to a flat end or melting to a rounded end) after the sidewalls are textured.

Figure 10:
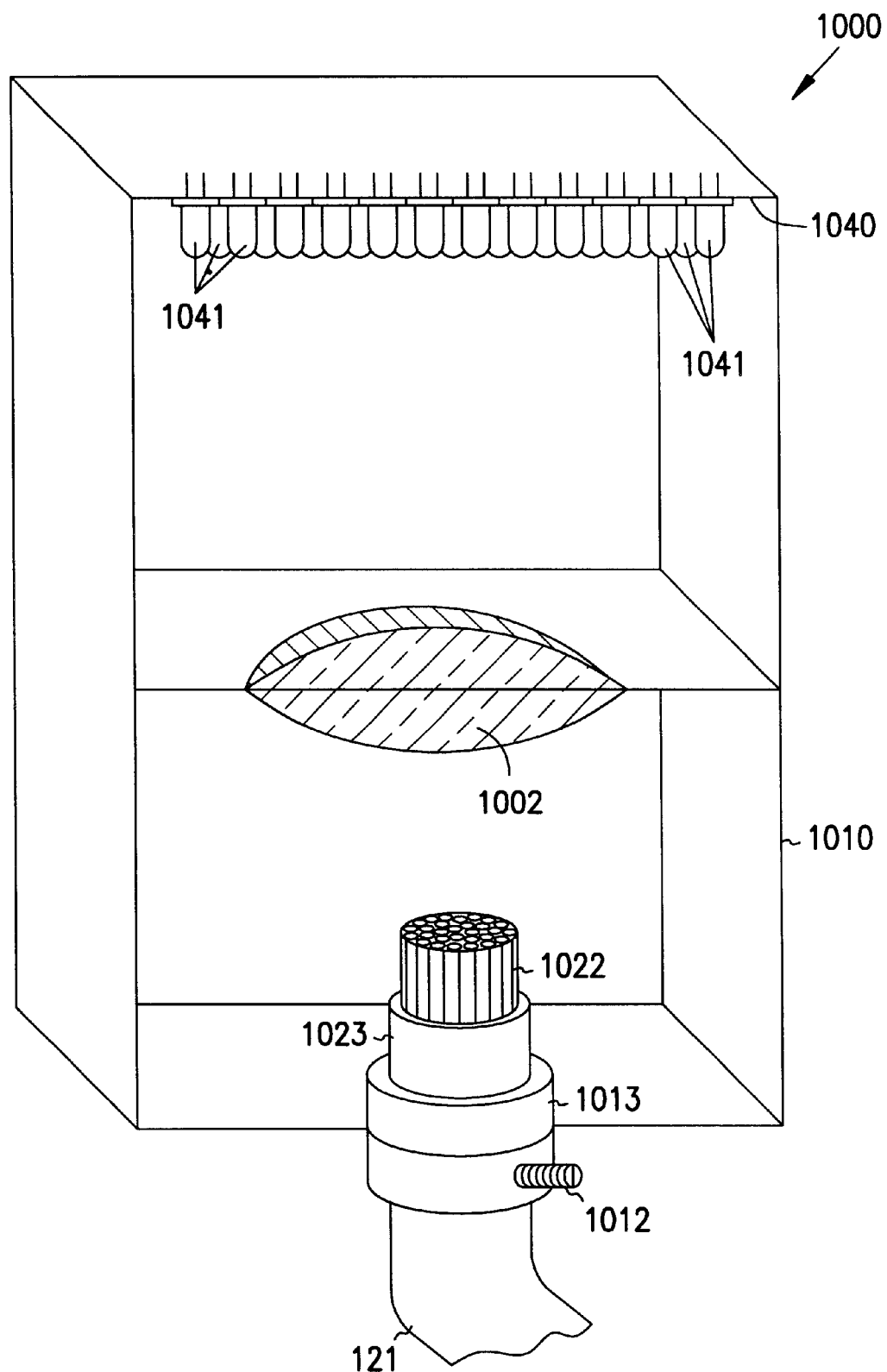
FIG. 10 is an isometric cross-section view of illumination source box 1010 according to one embodiment.

FIG. 10 is an isometric cross-section view of illumination system 1000, including source box 1010 according to another embodiment of the present invention. In this embodiment, a large plurality of individually tensed LEDs 1041 are mounted on a surface 1040. Surface 1040 is flat in one embodiment (shown in FIG. 10), and is concave in another embodiment (similar to that shown in FIG. 12). Optionally, lens 1002 further assists in focussing the light from LEDs 1041 onto the end 1122 of fiber bundle 121. In one embodiment, the ends and a short region of the sides of fibers in fiber bundle 121 are exposed to accept light. In the embodiment shown, a metal cylinder 1023 is permanently affixed to the end of fiber bundle 121, and fits into a corresponding cylinder 1013 that is permanently affixed to light box 1010. Set screw 1012 temporarily attaches the two. In one embodiment, a camera 130 and part-movement subsystem such as shown in FIG. 1 are also included in system 1000.

Figure 11:
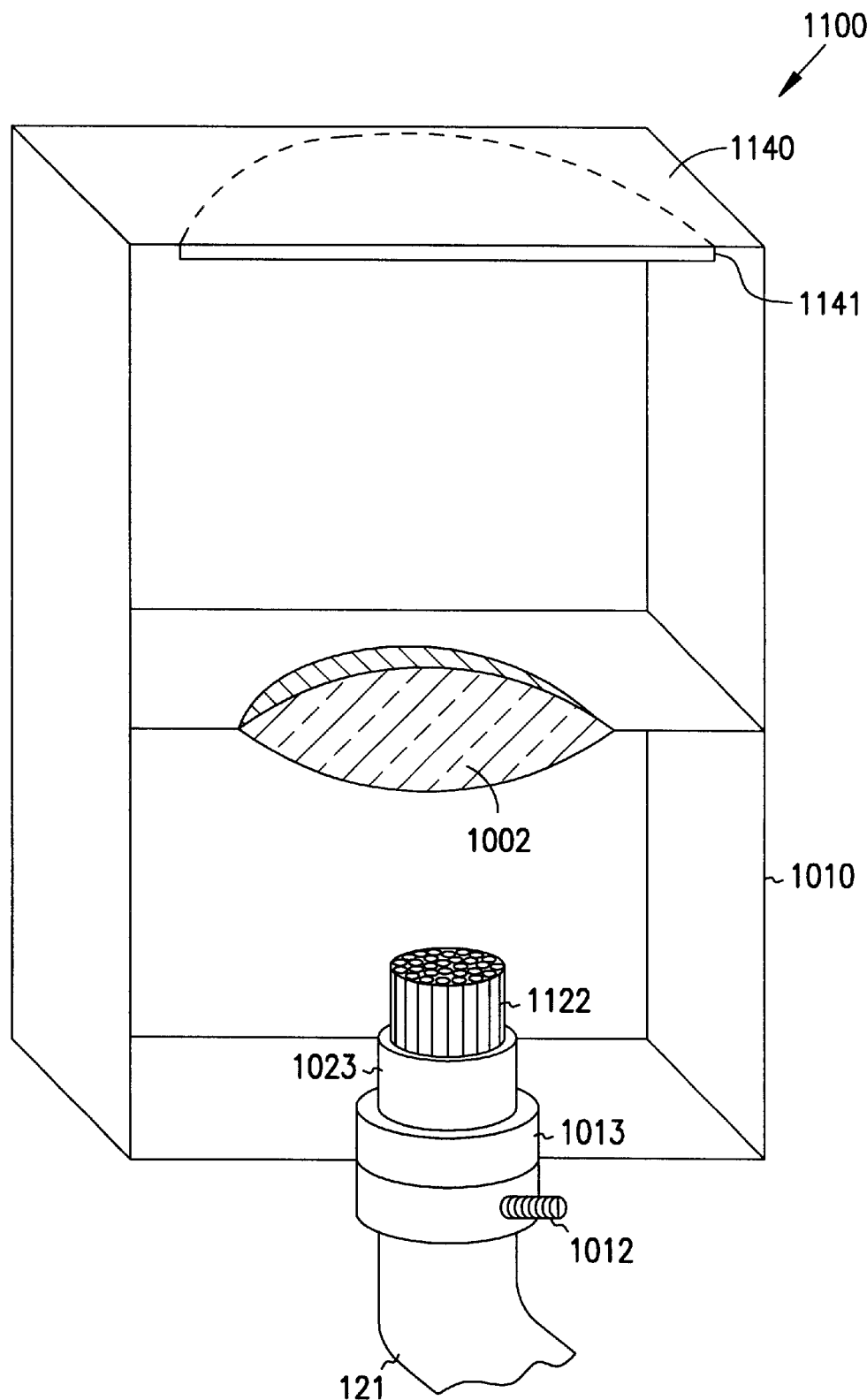
FIG. 11 is an isometric cross-section view of illumination source box 1110 according to one embodiment.

FIG. 11 is an isometric cross-section view of illumination system 1000, including illumination source box 1110 according to one embodiment. In this embodiment, a wafer or large portion thereof of LEDs 1141 are mounted on a surface 1140. In one embodiment (not shown), a heat sink and/or fan such as shown in FIG. 7 is mounted against surface 1140. Optionally, lens 1002 further assists in focussing the light from LED wafer 1141 onto the end 1122 of fiber bundle 121. In one embodiment, the ends and a short region of the sides of fibers in fiber bundle 121 are exposed to accept light. In the embodiment shown, a metal cylinder 1023 is permanently affixed to the end of fiber bundle 121, and fits into a corresponding cylinder 1013 that is permanently affixed to light box 1010. Set screw 1012 temporarily attaches the two. In one embodiment, a camera 130, computer and part-movement subsystem such as shown in FIG. 1 are also included in system 1100.

Figure 12:
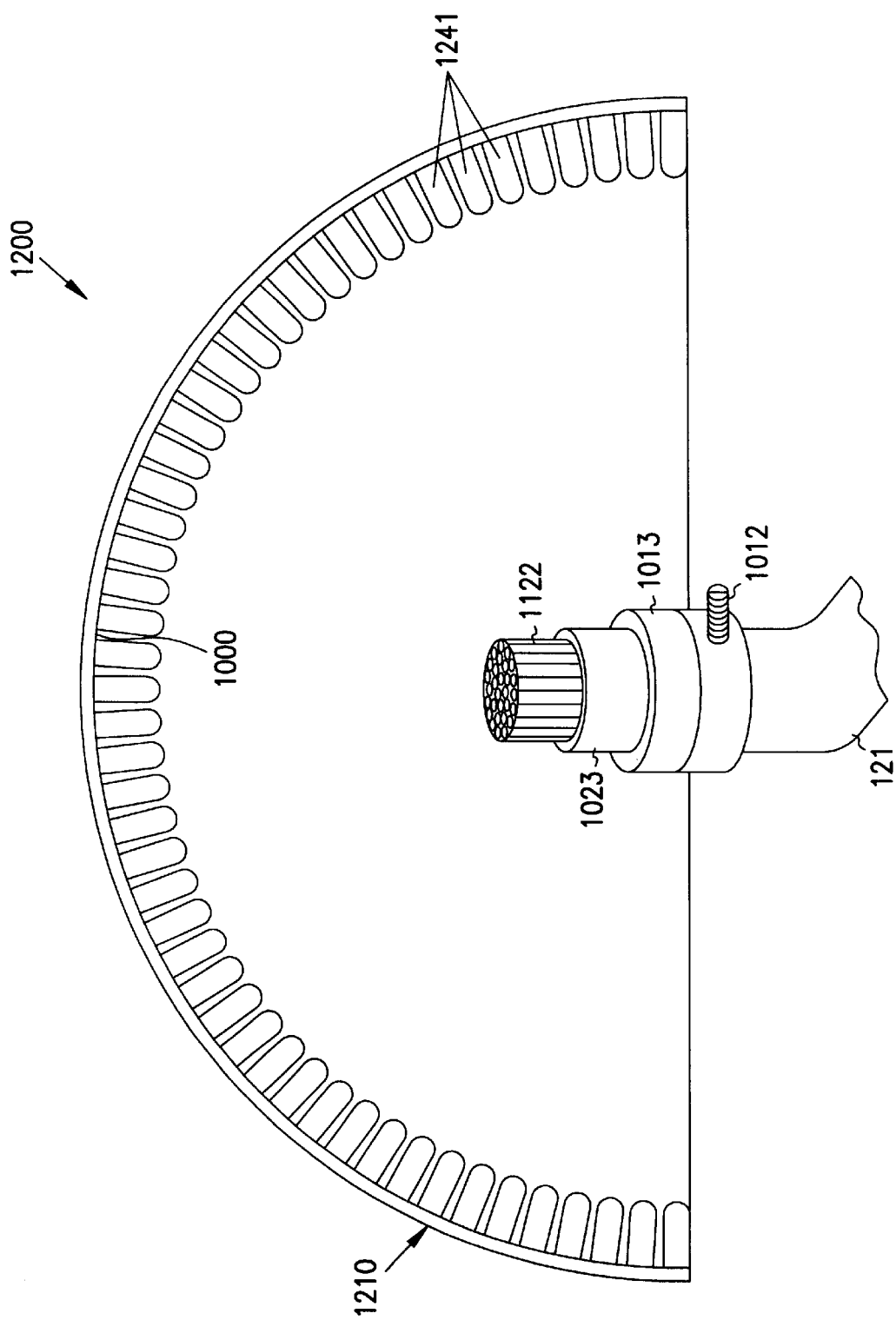
FIG. 12 is an isometric cross-section view of illumination source box 1210 according to one embodiment.

FIG. 12 is an isometric cross-section view of illumination system 1200, including light source box 1210 according to another embodiment of the present invention. In this embodiment, a large plurality of individually lensed LEDs 1041 are mounted on a concave surface 1240 (in one embodiment, surface 1240 is spherical and covered with LEDs 1241). In one embodiment, the ends and a short region of the sides 1122 of fibers in fiber bundle 121 are exposed to accept light. In the embodiment shown, a metal cylinder 1023 is permanently affixed to the end of fiber bundle 121, and fits into a corresponding cylinder 1013 that is permanently affixed to light box 1010. Set screw 1012 temporarily attaches the two. In one embodiment, a camera 130 and part-movement subsystem such as shown in FIG. 1 are also included in system 1200.

An illumination system is described in MACHINE-VISION ILLUMINATION SYSTEM AND METHOD, U.S. patent application Ser. No. 08/532,213, filed Oct. 12, 1995, and now U.S. Pat. No. 5,745,176 by Gary Lebens and assigned to PPT Vision, Inc., the assignee of the present invention, and which is hereby incorporated by reference. In one embodiment of the present invention, an LED power source and driver as described in Ser. No. 08/532,213 are used to drive the LEDs of the present invention.

A serial machine-vision interconnection system is described in HIGH-SPEED DIGITAL VIDEO SERIAL LINK, U.S. patent application Ser. No. 08/825,774, filed Apr. 02, 1997, which is a file-wrapper continuation of Ser. No. 08/410,119, filed Mar. 24, 1995 by Joseph C. Christianson and Larry G. Paulson and assigned to PPT Vision, Inc., the assignee of the present invention, and which is hereby incorporated by reference. In one embodiment of the present invention, a digital serial link such as described in Ser. No. 08/825,774 is used to control and drive the LEDs of the present invention.

The process of the present invention is unlike conventional illumination fixtures since it is compact, generates a light source from more than one point source with suitable brightness in order to reduce shadows, concentrates and focuses the light source into an output end 112 so optical-fiber bundles can be easily interchanged to provide improved flexibility of illumination for parts inspected and accurately viewed or measured with machine-vision system 100. Another aspect of the present invention is to provide a compact illumination fixture, preferably monochromatic, which can be concentrated to a fiber bundle to transmit the light onto all surfaces that are viewable by the machine vision camera. In one embodiment of the present invention, such an LED illumination source is pulsed with a relatively high-power, low duty-cycle power source. In another embodiment, continuous or controlled variation of light intensity is used.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. An illumination fixture for illuminating an object at a machine-vision station comprising:
    a plurality of light-emitting diode (LED) light sources;
    a fiber-optic assembly having a common first bundle end and plurality of second ends, wherein the common first end comprises a bundled arrangement of first ends of individual optical fibers, and the second ends are optically coupled to receive light from the plurality of LEDs, and the second ends are in fiber-optic communication with the common first bundle end such that substantially all light in the fiber-optic assembly from the LEDs is output and leaves the fixture at the bundled first ends of individual fibers; and
    a plurality of pipe cells, wherein each one of the plurality of LED light sources is associated with a respective pipe cell that serves to focus light from its LED light source into one or more of the fibers.

2. The illumination fixture according to claim 1, wherein each of the pipe cells includes a focussing reflective surface.

3. The illumination fixture according to claim 1, wherein each of the pipe cells includes a concave substantially spherical focussing reflective surface.

4. The illumination fixture according to claim 1, wherein each of the pipe cells includes a focussing lens that focusses light emitted from its LED on a fiber end.

5. An illumination system for illuminating an object at a machine-vision station comprising:
    an illumination fixture including:
        a substantially closed housing having a light-output terminal;
        a plurality of light-emitting diode (LED) light sources within the housing; and
        an internal fiber-optic assembly having a common first bundle end and plurality of second ends, each one of the second ends optically coupled to receive light from one of the plurality of LEDs, and all of the second ends in fiber-optic communication with the common first end, and the fiber-optic assembly held substantially within the housing such that light from the LEDs is output from the fixture at the first bundle end located at the light-output terminal, wherein each one of the second ends is a ball end formed by melting.

6. The illumination fixture according to claim 1, wherein each of the pipe cells includes a substantially cylindrical interior reflective surface.

7. The illumination fixture according to claim 1, wherein each of the pipe cells includes an hourglass-shaped interior reflective surface.

8. The illumination fixture according to claim 1, wherein each of the pipe cells includes a substantially spherical interior reflective surface.

9. The illumination fixture according to claim 8, wherein each of the second fiber ends in the pipe cells includes a substantially spherical fiber-end surface.

10. The illumination fixture according to claim 1, wherein each of the pipe cells is filled with a light-transmissive material.

11. The illumination fixture according to claim 1, wherein each of the pipe cells is filled with a light-transmissive plastic.

12. The illumination fixture according to claim 1, wherein the plurality of LEDs are arranged in a plurality of rows, each row having a plurality of LEDs, and each of the pipe cells is part of one row of a plurality of separate rows of pipe cells, each row of pipe cells associated with one row of LEDs, such that each row of pipe cells can be assembled to a plurality of fibers, and then affixed to a row of LEDs.

13. A method for illuminating an object at a machine-vision station, comprising:

(a) providing a first plurality of optical fibers each having a first end and a second end and a separate plurality of optical fibers each having a first end and a second end, wherein all of the first ends of the first plurality of optical fibers are grouped into a compact bundle end, and all of the first ends of the second plurality of optical fibers are grouped into a compact bundle end;

(b) emitting light from a plurality of LEDs onto the second ends individual ones of the first plurality of optical fibers;

(c) coupling light from the compact bundle end of the first plurality of optical fibers into the compact bundle end of the separate second plurality of optical fibers;

(d) emitting light from the second ends of the second plurality of optical fibers to the object at the machine-vision station; and (e) imaging the light from the object into a machine-vision imaging device.

14. The method according to claim 13, further comprising optically coupling light from each one of the plurality of LEDs into one of the second ends of a corresponding one of the fibers.

15. The method according to claim 14, further comprising:

terminating each fiber at the first end of the first plurality of optical fibers at a common plane and terminating each fiber at the first end of the second plurality of optical fibers at a common plane.

16. The method according to claim 14, further comprising:

locating each fiber randomly within the bundle at the first end.

17. The method according to claim 14, further comprising focussing light from each LED into one or more of the fibers using a pipe cell, wherein each LED is associated with a respective pipe cell.

18. The method according to claim 17, wherein each of the pipe cells includes a focussing reflective surface.

19. The method according to claim 17, wherein each of the pipe cells includes a concave substantially spherical focussing reflective surface.

20. The method according to claim 17, wherein each of the pipe cells includes a focussinig lens that focusses light emitted from its LED on a fiber end.

21. The method according to claim 14, further comprising:

coupling light from the first bundle end of the first plurality of optical fibers into one of a plurality of interchangeably connected fiber-bundle head fixtures.

22. The method according to claim 14, further comprising coupling heat from the plurality of LEDs to a heat sink.

23. A machine-vision system for obtaining information about an object at a machine-vision station, comprising:

an imaging device;

an image processor coupled to the imaging device; and an illumination source coupled to the image processor, the illumination source comprising:

a plurality of light-emitting diode (LED) light sources;

a fiber-optic assembly having a common first bundle end and plurality of second ends, each one of the second ends optically coupled to receive light from one of the plurality of LEDs, and all of the second ends in fiber-optic communication with the common first end such that light from the LEDs is output at the first end;

a coupling unit attached to the first bundle end adapted to receive one of a plurality of interchangeably connected fiber-bundle head fixtures and to transmit light from the first bundle end output into one of the plurality of interchangeably connected fiber-bundle head fixtures; and a fiber-bundle head fixture adapted transmit light received at the coupling unit to the object at the machine vision station.

24. The machine-vision system according to claim 23, wherein each fiber is randomly located within the bundle at the first end.

25. The machine-vision system according to claim 23, further comprising a plurality of pipe cells, wherein each LED is associated with a respective pipe cell that serves to focus light from the LED into one or more of the fibers.

26. The machine-vision system according to claim 23, wherein each of the pipe cells includes a concave focussing reflective surface.

27. The machine-vision system according to claim 26, wherein each of the pipe cells includes a focussing lens that focusses light emitted from its LED on a fiber end.

* * * * *